United States Patent
Nam et al.

(10) Patent No.: US 10,364,289 B2
(45) Date of Patent: Jul. 30, 2019

(54) ANTIBODY BINDING TO NEUROPILIN 1 AND USE THEREOF

(71) Applicant: SAMSUNG LIFE PUBLIC WELFARE FOUNDATION, Seoul (KR)

(72) Inventors: Do-Hyun Nam, Seoul (KR); Yeup Yoon, Seoul (KR); Jae Hyun Lee, Gyeonggi-do (KR); Jin Ku Lee, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 162 days.

(21) Appl. No.: 15/532,078

(22) PCT Filed: Dec. 3, 2015

(86) PCT No.: PCT/KR2015/013102
§ 371 (c)(1),
(2) Date: May 31, 2017

(87) PCT Pub. No.: WO2016/089126
PCT Pub. Date: Jun. 9, 2016

(65) Prior Publication Data
US 2017/0291948 A1    Oct. 12, 2017

(30) Foreign Application Priority Data

Dec. 3, 2014 (KR) .......................... 10-2014-0171949

(51) Int. Cl.
*C07K 16/00* (2006.01)
*C07K 16/28* (2006.01)
*A61K 39/395* (2006.01)
*A61K 47/68* (2017.01)
*A61K 39/00* (2006.01)

(52) U.S. Cl.
CPC ........ *C07K 16/2863* (2013.01); *A61K 39/395* (2013.01); *A61K 47/6849* (2017.08); *C07K 16/28* (2013.01); *A61K 2039/505* (2013.01); *C07K 2317/56* (2013.01); *C07K 2317/565* (2013.01); *C07K 2317/567* (2013.01); *C07K 2317/622* (2013.01); *C07K 2317/77* (2013.01); *C07K 2317/92* (2013.01)

(58) Field of Classification Search
CPC ..................................................... C07K 16/00
USPC ..................................................... 530/387.1
See application file for complete search history.

(56) References Cited

U.S. PATENT DOCUMENTS

| | | |
|---|---|---|
| 2009/0226372 A1 | 9/2009 | Ruoslahti et al. |
| 2010/0322862 A1 | 12/2010 | Ruoslahti et al. |
| 2016/0130315 A1 | 5/2016 | Kim et al. |

FOREIGN PATENT DOCUMENTS

| | | |
|---|---|---|
| CA | 2313607 A1 | 12/1998 |
| EP | 1442749 A1 | 8/2004 |
| JP | 2004526940 A | 9/2004 |
| JP | 2006516594 A | 7/2006 |
| JP | 2012530787 A | 12/2012 |
| KR | 10-2012-0048563 A | 5/2012 |
| WO | 8801649 A1 | 3/1988 |
| WO | 8806630 A1 | 9/1988 |
| WO | 8807085 A1 | 9/1988 |
| WO | 8807086 A1 | 9/1988 |
| WO | 8809344 A1 | 12/1988 |
| WO | 0136487 A2 | 5/2001 |
| WO | WO0233044 A2 | 4/2002 |
| WO | 2007019406 A2 | 2/2007 |
| WO | 2011143408 A1 | 11/2011 |
| WO | WO2014150314 A1 | 9/2014 |
| WO | WO2014189303 A1 | 11/2014 |

OTHER PUBLICATIONS

Liang et al (J. Mol. Biol., 2007, 366: 815-829).*
Manjappa et al (Journal of Drug Targeting, 2014, 22(8): 698-711).*
Schrappe et al (Cancer Research, 1992, 52: 3838-3844).*
Patnaik, A., et al., "A Phase Ib study evaluating MNRP1685A, a fully human anti-NRP1 monoclonal antibody, in combination with bevacizumab and paclitaxel in patients with advanced solid tumors", "Cancer Chemother Pharmacol", Mar. 17, 2014, pp. 951-960, vol. 73, Publisher: Springer-Verlag Berlin Heidelberg 2014.
Ruffini, F., et al, "Neuropilin-1 expression promotes invasiveness of melanoma cells through vascular endothelial growth factor receptor-2-dependent and -independent mechanisms", "International Journal of Oncology", Jan. 28, 2013, pp. 297-306, vol. 43.
Weekes, C., et al., "A phase I study of the human nonoclonal anti-NRP1 antibody MNRP1685A in patients with advanced solid tumors", "Invest New Drugs", Mar. 7, 2014, pp. 653-660, vol. 32, Publisher: Springer Science + Business Media New York 2014.
Bumbaca, D., et al., "Maximizing Tumour Exposure to Anti-Neuropilin-1 Antibody Requires Saturation of Non-Tumour Tissue Antigenic Sinks in Mice", "British Journal of Pharmacology", 2012, pp. 368-377, vol. 166.

(Continued)

*Primary Examiner* — Sean E Aeder

(74) *Attorney, Agent, or Firm* — Hultquist, PLLC; Steven J. Hultquist

(57) ABSTRACT

The present disclosure relates to an antibody binding to Neuropilin 1 (NRP1) or an antigen-binding fragment thereof, a nucleic acid encoding the same, a vector comprising the nucleic acid, a cell transformed with the vector, a method for preparing the antibody or the antigen-binding fragment thereof, an antibody-drug conjugate comprising the antibody or the antigen-binding fragment thereof, and a composition thereof for preventing or treating a cancer.

11 Claims, 24 Drawing Sheets

(21 of 24 Drawing Sheet(s) Filed in Color)

Specification includes a Sequence Listing.

(56) References Cited

OTHER PUBLICATIONS

Prudhomme, G., et al., "Neuropilins are Multifunctional Coreceptors Involved in Tumor Initiation, Growth, Metastasis and Immunity", "Oncotarget", 2012, pp. 921-939, vol. 3, No. 9.

Roth, L., et al., "Transtumoral targeting enabled by a novel neuropilin-binding peptide", "Oncogene", Dec. 19, 2011, pp. 3754-3763, vol. 31.

Sugahara, K.N., et al., "Tissue-penetrating delivery of compounds and nanoparticles into tumors", "Cancer Cell", Dec. 8, 2009, pp. 510-520, vol. 16, No. 6.

Yang, H.Y., et al., "Construction of a Large Synthetic Human scFv Library with Six Diversified CDRs and High Functional Diversity", "Molecules and Cells", Feb. 28, 2009, pp. 225-235, vol. 27.

* cited by examiner

SEQUENCE LISTING

```
<160> NUMBER OF SEQ ID NOS: 42

<210> SEQ ID NO 1
<211> LENGTH: 8
<212> TYPE: PRT
<213> ORGANISM: Artificial Sequence
<220> FEATURE:
<223> OTHER INFORMATION: CDRH1 of 4F12

<400> SEQUENCE: 1

Gly Phe Thr Phe Ser Gly Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: CDRH2 of 4F12

<400> SEQUENCE: 2
```

Ile Ser Pro Gly Ser Gly Ser Thr
1               5

<210> SEQ ID NO 3
<211> LENGTH: 9
<212> TYPE: PRT
<213> ORGANISM: Artificial Sequence
<220> FEATURE:
<223> OTHER INFORMATION: CDRH3 of 4F12

<400> SEQUENCE: 3

Ala Lys Arg Lys Thr Arg Phe Asp Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: CDRL1 of 4F12

<400> SEQUENCE: 4

Ser Ser Asn Ile Gly Asn Asn Ser
1               5

<210> SEQ ID NO 5

<400> SEQUENCE: 5

000

<210> SEQ ID NO 6
<211> LENGTH: 11
<212> TYPE: PRT
<213> ORGANISM: Artificial Sequence
<220> FEATURE:
<223> OTHER INFORMATION: CDRL3 of 4F12

<400> SEQUENCE: 6

Ala Ala Trp Asp Ser Ser Leu Asn Gly Tyr Val
1               5                   10

<210> SEQ ID NO 7
<211> LENGTH: 8
<212> TYPE: PRT
<213> ORGANISM: Artificial Sequence
<220> FEATURE:
<223> OTHER INFORMATION: CDRH1 of 1A03 or 3H10

<400> SEQUENCE: 7

Gly Phe Thr Phe Ser Ser Tyr Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: CDRH2 of 1A03 or 3H10

<400> SEQUENCE: 8

Ile Ser Pro Gly Ser Ser Asn Lys
1               5

<210> SEQ ID NO 9
<211> LENGTH: 9
<212> TYPE: PRT

-continued

```
<213> ORGANISM: Artificial Sequence
<220> FEATURE:
<223> OTHER INFORMATION: CDRH3 of 1A03

<400> SEQUENCE: 9

Ala Arg Arg Lys Lys Ser Phe Asp Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: CDRL1 of 1A03 or 3H10

<400> SEQUENCE: 10

Ser Ser Asn Ile Gly Asn Asn Asp
1               5

<210> SEQ ID NO 11

<400> SEQUENCE: 11

000

<210> SEQ ID NO 12
<211> LENGTH: 11
<212> TYPE: PRT
<213> ORGANISM: Artificial Sequence
<220> FEATURE:
<223> OTHER INFORMATION: CDRL3 of 1A03

<400> SEQUENCE: 12

Gly Ala Trp Val Ala Ser Leu Ser Ala Tyr Val
1               5                   10

<210> SEQ ID NO 13
<211> LENGTH: 9
<212> TYPE: PRT
<213> ORGANISM: Artificial Sequence
<220> FEATURE:
<223> OTHER INFORMATION: CDRH3 of 3H10

<400> SEQUENCE: 13

Ala Arg Arg Lys Tyr Met Phe Asp Tyr
1               5

<210> SEQ ID NO 14

<400> SEQUENCE: 14

000

<210> SEQ ID NO 15
<211> LENGTH: 11
<212> TYPE: PRT
<213> ORGANISM: Artificial Sequence
<220> FEATURE:
<223> OTHER INFORMATION: CDRL3 of 3H10

<400> SEQUENCE: 15

Ala Ser Trp Asp Ser Ser Leu Ser Gly Tyr Val
1               5                   10

<210> SEQ ID NO 16
<211> LENGTH: 116
<212> TYPE: PRT
```

<213> ORGANISM: Artificial Sequence
<220> FEATURE:
<223> OTHER INFORMATION: VH of 4F12

<400> SEQUENCE: 16

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Gly Ile Ser Pro Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Lys Thr Arg Phe Asp Tyr Trp Gly Gln Gly Thr Leu Val
            100                 105                 110

Thr Val Ser Ser
        115
```

<210> SEQ ID NO 17
<211> LENGTH: 110
<212> TYPE: PRT
<213> ORGANISM: Artificial Sequence
<220> FEATURE:
<223> OTHER INFORMATION: VL of 4F12

<400> SEQUENCE: 17

```
Gln Ser Val Leu Thr Gln Pro Pro Ser Ala Ser Gly Thr Pro Gly Arg
 1               5                  10                  15

Arg Val Thr Ile Ser Cys Ser Gly Ser Ser Ser Asn Ile Gly Asn Asn
            20                  25                  30

Ser Val Tyr Trp Tyr Gln Gln Leu Pro Gly Thr Ala Pro Lys Leu Leu
        35                  40                  45

Ile Tyr Ala Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Asn Gly Tyr Val Phe Gly Gly Gly Thr Lys Leu Thr Val Leu
            100                 105                 110
```

<210> SEQ ID NO 18
<211> LENGTH: 116
<212> TYPE: PRT
<213> ORGANISM: Artificial Sequence
<220> FEATURE:
<223> OTHER INFORMATION: VH of 1A03

<400> SEQUENCE: 18

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45
```

```
Ser Ala Ile Ser Pro Gly Ser Ser Asn Lys Tyr Tyr Ala Asp Ser Val
        50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Lys Lys Ser Phe Asp Tyr Trp Gly Gln Gly Thr Leu Val
            100                 105                 110

Thr Val Ser Ser
            115

<210> SEQ ID NO 19
<211> LENGTH: 110
<212> TYPE: PRT
<213> ORGANISM: Artificial Sequence
<220> FEATURE:
<223> OTHER INFORMATION: VL of 1A03

<400> SEQUENCE: 19

Gln Ser Val Leu Thr Gln Pro Pro Ser Ala Ser Gly Thr Pro Gly Gln
1               5                   10                  15

Arg Val Thr Ile Ser Cys Ser Gly Pro Ser Ser Asn Ile Gly Asn Asn
                20                  25                  30

Asp Val Ser Trp Tyr Gln Gln Leu Pro Gly Thr Ala Pro Lys Leu Leu
            35                  40                  45

Ile Tyr Ser Asp Asn Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Val Ala Ser Leu
                85                  90                  95

Ser Ala Tyr Val Phe Gly Gly Gly Thr Lys Leu Thr Val Leu
            100                 105                 110

<210> SEQ ID NO 20
<211> LENGTH: 116
<212> TYPE: PRT
<213> ORGANISM: Artificial Sequence
<220> FEATURE:
<223> OTHER INFORMATION: VH of 3H10

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Tyr Met Ser Trp Val Arg Gln Ala Pro Gly Lys Gly Leu Glu Trp Val
            35                  40                  45

Ser Ala Ile Ser Pro Gly Ser Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Lys Tyr Met Phe Asp Tyr Trp Gly Gln Gly Thr Leu Val
            100                 105                 110

Thr Val Ser Ser
```

<210> SEQ ID NO 21
<211> LENGTH: 110
<212> TYPE: PRT
<213> ORGANISM: Artificial Sequence
<220> FEATURE:
<223> OTHER INFORMATION: VL of 3H10

<400> SEQUENCE: 21

```
Gln Ser Val Leu Thr Gln Pro Pro Ser Ala Ser Gly Thr Pro Gly Gln
1               5                   10                  15
Arg Val Thr Ile Ser Cys Thr Gly Ser Ser Ser Asn Ile Gly Asn Asn
            20                  25                  30
Asp Val Tyr Trp Tyr Gln Gln Leu Pro Gly Thr Ala Pro Lys Leu Leu
        35                  40                  45
Ile Tyr Ser Asp Ser Asn Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ser Trp Asp Ser Ser Leu
                85                  90                  95
Ser Gly Tyr Val Phe Gly Gly Gly Thr Lys Leu Thr Val Leu
            100                 105                 110
```

<210> SEQ ID NO 22
<211> LENGTH: 348
<212> TYPE: DNA
<213> ORGANISM: Artificial Sequence
<220> FEATURE:
<223> OTHER INFORMATION: VH of 4F12

<400> SEQUENCE: 22

```
gaggtgcagc tgttggagtc tgggggaggc ttggtacagc ctgggggtc cctgagactc      60
tcctgtgcag cctctggatt caccttagc ggttatgcta tgagctgggt ccgccaggct    120
ccagggaagg ggctggagtg ggtctcaggg atctctcctg gtagtggtag tacatattac    180
gctgattctg taaaaggtcg gttcaccatc tccagagaca attccaagaa cacgctgtat    240
ctgcaaatga acagcctgag agccgaggac acggccgtgt attactgtgc gaaacgtaag    300
actaggttcg actactgggg ccagggtaca ctggtcaccg tgagctca                  348
```

<210> SEQ ID NO 23
<211> LENGTH: 330
<212> TYPE: DNA
<213> ORGANISM: Artificial Sequence
<220> FEATURE:
<223> OTHER INFORMATION: VL of 4F12

<400> SEQUENCE: 23

```
cagtctgtgc tgactcagcc accctcagcg tctgggaccc ccgggcggag ggtcaccatc      60
tcttgtagtg gctcttcatc taatattggc aataattctg tctactggta ccagcagctc    120
ccaggaacgg ccccaaaact cctcatctat gctaataata gcggccaag cggggtccct     180
gaccgattct ctggctccaa gtctggcacc tcagcctccc tggccatcag tgggctccgg    240
tccgaggatg aggctgatta ttactgtgct gcttgggatt ctagcctgaa tggttatgtc    300
ttcggcggag gcaccaagct gacggtccta                                      330
```

<210> SEQ ID NO 24

```
<211> LENGTH: 348
<212> TYPE: DNA
<213> ORGANISM: Artificial Sequence
<220> FEATURE:
<223> OTHER INFORMATION: VH of 1A03

<400> SEQUENCE: 24
gaggtgcagc tgttggagtc tgggggaggc ttggtacagc ctggggggtc cctgagactc      60
tcctgtgcag cctctggatt cacctttagc agttattata tgagctgggt ccgccaggct     120
ccagggaagg ggctggagtg ggtctcagcg atctctcctg gtagtagtaa taaatattac     180
gctgattctg tacaaggtcg gttcaccatc tccagagaca attccaagaa cacgctgtat     240
ctgcaaatga acagcctgag agccgaggac acggccgtgt attactgtgc gagaaggaag     300
aagtcgttcg actactgggg ccagggtaca ctggtcaccg tgagctca                  348

<210> SEQ ID NO 25
<211> LENGTH: 330
<212> TYPE: DNA
<213> ORGANISM: Artificial Sequence
<220> FEATURE:
<223> OTHER INFORMATION: VL of 1A03

<400> SEQUENCE: 25
cagtctgtgc tgactcagcc accctcagcg tctgggaccc ccgggcagag ggtcaccatc      60
tcttgtagtg gccttcatc taatattggc aataatgatg tctcctggta ccagcagctc     120
ccaggaacgg ctcccaaact cctcatctat tctgataata atcggccaag cggggtccct     180
gaccgattct ctggctccaa gtctggcacc tcagcctccc tggccatcag tgggctccgg     240
tccgaggatg aggctgatta ttactgtggt gcttgggttg ctagcctgag tgcttatgtc     300
ttcggcggag gcaccaagct gacggtccta                                       330

<210> SEQ ID NO 26
<211> LENGTH: 348
<212> TYPE: DNA
<213> ORGANISM: Artificial Sequence
<220> FEATURE:
<223> OTHER INFORMATION: VH of 3H10

<400> SEQUENCE: 26
gaggtgcagc tgttggagtc tgggggaggc ttggtacagc ctggggggtc cctgagactc      60
tcctgtgcag cctctggatt cacctttagc agttattata tgagctgggt ccgccaggct     120
ccagggaagg ggctggagtg ggtctcagcg atctctcctg gtagtagtaa taaatattac     180
gctgattctg taaaaggtcg gttcaccatc tccagagaca attccaagaa cacgctgtat     240
ctgcaaatga acagcctgag agccgaggac acggccgtgt attactgtgc gagaaggaag     300
tatatgttcg actactgggg ccagggtaca ctggtcaccg tgagctca                  348

<210> SEQ ID NO 27
<211> LENGTH: 330
<212> TYPE: DNA
<213> ORGANISM: Artificial Sequence
<220> FEATURE:
<223> OTHER INFORMATION: VL of 3H10

<400> SEQUENCE: 27
cagtctgtgc tgactcagcc accctcagcg tctgggaccc ccgggcagag ggtcaccatc      60
tcttgtactg gctcttcatc taatattggc aataatgatg tctactggta ccagcagctc     120
ccaggaacgg cacccaaact cctcatctat tctgatagta atcggccaag cggggtccct     180
```

```
gaccgattct ctggctccaa gtctggcacc tcagcctccc tggccatcag tgggctccgg    240
tccgaggatg aggctgatta ttactgtgct tcttgggatt ctagcctgag tggttatgtc    300
ttcggcggag gcaccaagct gacggtccta                                     330
```

```
<210> SEQ ID NO 28
<211> LENGTH: 25
<212> TYPE: PRT
<213> ORGANISM: Artificial Sequence
<220> FEATURE:
<223> OTHER INFORMATION: 1A03, 3H10 & 4F12 Hv FR1

<400> SEQUENCE: 28
```

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

```
<210> SEQ ID NO 29
<211> LENGTH: 17
<212> TYPE: PRT
<213> ORGANISM: Artificial Sequence
<220> FEATURE:
<223> OTHER INFORMATION: 1A03 & 3H10 Hv FR2

<400> SEQUENCE: 29
```

Met Ser Trp Val Arg Gln Ala Pro Gly Lys Gly Leu Glu Trp Val Ser
1               5                   10                  15

Ala

```
<210> SEQ ID NO 30
<211> LENGTH: 17
<212> TYPE: PRT
<213> ORGANISM: Artificial Sequence
<220> FEATURE:
<223> OTHER INFORMATION: 4F12 Hv FR2

<400> SEQUENCE: 30
```

Met Ser Trp Val Arg Gln Ala Pro Gly Lys Gly Leu Glu Trp Val Ser
1               5                   10                  15

Gly

```
<210> SEQ ID NO 31
<211> LENGTH: 38
<212> TYPE: PRT
<213> ORGANISM: Artificial Sequence
<220> FEATURE:
<223> OTHER INFORMATION: 1A03 Hv FR3

<400> SEQUENCE: 31
```

Tyr Tyr Ala Asp Ser Val Gln Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

```
<210> SEQ ID NO 32
<211> LENGTH: 38
<212> TYPE: PRT
<213> ORGANISM: Artificial Sequence
<220> FEATURE:
<223> OTHER INFORMATION: 3H10 & 4F12 Hv FR3
```

<400> SEQUENCE: 32

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
            35

<210> SEQ ID NO 33
<211> LENGTH: 11
<212> TYPE: PRT
<213> ORGANISM: Artificial Sequence
<220> FEATURE:
<223> OTHER INFORMATION: 1A03, 3H10 & 4F12 Hv FR4

<400> SEQUENCE: 33

Trp Gly Gln Gly Thr Leu Val Thr Val Ser Ser
1               5                   10

<210> SEQ ID NO 34
<211> LENGTH: 25
<212> TYPE: PRT
<213> ORGANISM: Artificial Sequence
<220> FEATURE:
<223> OTHER INFORMATION: 1A03 Lv FR1

<400> SEQUENCE: 34

Gln Ser Val Leu Thr Gln Pro Pro Ser Ala Ser Gly Thr Pro Gly Gln
1               5                   10                  15

Arg Val Thr Ile Ser Cys Ser Gly Pro
            20                  25

<210> SEQ ID NO 35
<211> LENGTH: 25
<212> TYPE: PRT
<213> ORGANISM: Artificial Sequence
<220> FEATURE:
<223> OTHER INFORMATION: 3H10 Lv FR1

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Thr Gly Ser
            20                  25

<210> SEQ ID NO 36
<211> LENGTH: 25
<212> TYPE: PRT
<213> ORGANISM: Artificial Sequence
<220> FEATURE:
<223> OTHER INFORMATION: 4F12 Lv FR1

<400> SEQUENCE: 36

Gln Ser Val Leu Thr Gln Pro Pro Ser Ala Ser Gly Thr Pro Gly Arg
1               5                   10                  15

Arg Val Thr Ile Ser Cys Ser Gly Ser
            20                  25

<210> SEQ ID NO 37
<211> LENGTH: 17
<212> TYPE: PRT
<213> ORGANISM: Artificial Sequence
<220> FEATURE:

<223> OTHER INFORMATION: 1A03 Lv FR2

<400> SEQUENCE: 37

Val Ser Trp Tyr Gln Gln Leu Pro Gly Thr Ala Pro Lys Leu Leu Ile
1               5                   10                  15

Tyr

<210> SEQ ID NO 38
<211> LENGTH: 17
<212> TYPE: PRT
<213> ORGANISM: Artificial Sequence
<220> FEATURE:
<223> OTHER INFORMATION: 3H10 Lv FR2

<400> SEQUENCE: 38

Val Tyr Trp Tyr Gln Gln Leu Pro Gly Thr Ala Pro Lys Leu Leu Ile
1               5                   10                  15

Tyr

<210> SEQ ID NO 39
<211> LENGTH: 17
<212> TYPE: PRT
<213> ORGANISM: Artificial Sequence
<220> FEATURE:
<223> OTHER INFORMATION: 4F12 Lv FR2

<400> SEQUENCE: 39

Val Tyr Trp Tyr Gln Gln Leu Pro Gly Thr Ala Pro Lys Leu Leu Ile
1               5                   10                  15

Tyr

<210> SEQ ID NO 40
<211> LENGTH: 36
<212> TYPE: PRT
<213> ORGANISM: Artificial Sequence
<220> FEATURE:
<223> OTHER INFORMATION: 1A03 & 3H10 Lv FR3

<400> SEQUENCE: 40

Asn Arg Pro Ser Gly Val Pro Asp Arg Phe Ser Gly Ser Lys Ser Gly
1               5                   10                  15

Thr Ser Ala Ser Leu Ala Ile Ser Gly Leu Arg Ser Glu Asp Glu Ala
                20                  25                  30

Asp Tyr Tyr Cys
            35

<210> SEQ ID NO 41
<211> LENGTH: 36
<212> TYPE: PRT
<213> ORGANISM: Artificial Sequence
<220> FEATURE:
<223> OTHER INFORMATION: 4F12 Lv FR3

<400> SEQUENCE: 41

Lys Arg Pro Ser Gly Val Pro Asp Arg Phe Ser Gly Ser Lys Ser Gly
1               5                   10                  15

Thr Ser Ala Ser Leu Ala Ile Ser Gly Leu Arg Ser Glu Asp Glu Ala
                20                  25                  30

Asp Tyr Tyr Cys
            35

<210> SEQ ID NO 42

```
<211> LENGTH: 10
<212> TYPE: PRT
<213> ORGANISM: Artificial Sequence
<220> FEATURE:
<223> OTHER INFORMATION: 1A03, 3H10 & 4F12 Lv FR4

<400> SEQUENCE: 42

Phe Gly Gly Gly Thr Lys Leu Thr Val Leu
1               5                   10
```

ANTIBODY BINDING TO NEUROPILIN 1 AND USE THEREOF

CROSS-REFERENCE TO RELATED APPLICATIONS

This application is a U.S. national phase under the provisions of 35 U.S.C. § 371 of International Patent Application No. PCT/KR2015/013102 filed Dec. 3, 2015, which in turn claims priority of Korean Patent Application No. 10-2014-0171949 filed Dec. 3, 2014. The disclosures of such international patent application and Korean priority patent application are hereby incorporated herein by reference in their respective entireties, for all purposes.

BACKGROUND

Field

The present disclosure relates to an antibody binding to neuropilin 1 (NRP1) or an antigen-binding fragment thereof, a nucleic acid encoding the same, a vector including the nucleic acid, a cell transformed with the vector, a method for preparing the antibody or the antigen-binding fragment thereof, an antibody-drug conjugate including the antibody or the antigen-binding fragment thereof, and a composition thereof for preventing or treating a cancer.

Description of the Related Art

Neuropilin (NRP) includes NRP1 and NRP2, which was first discovered in the nerve cells. It was known that NRP1 is composed of about 923 amino acids and NRP2 is composed of about 926 amino acids. Further, they have a similar domain structure in common and thus have an amino acid homology of 44% in total.

NRP1 is known as a receptor binding to the semaphorin 3A ligand, which acts on the plexin adjuvant-receptor to adjust axonal induction. It has then been found that NRP1 is bound to members of the vascular endothelial growth factor (VEGF) ligand family and thus mediates angiogenesis.

Numerous physiological processes and pathological processes occur through the development of the vascular system. Blood must be adequately supplied to actively growing tissues such as a tumor. These tissues typically produce pro-angiogenic factors that promote new blood vessel formation and maintenance so as to supply blood through angiogenesis. Angiogenesis is not a simple process, but is accomplished through the following steps that: a) endothelial cells (EC) are proliferated or differentiated from existing endothelial cells; b) endothelial cells migrate and coalesce to form a cord-like structure; c) the blood vessel cord progresses tubule formation and forms a vessel having a lumen in the center; d) buds of existing cords or blood vessels begin to form secondary blood vessels; e) the primitive plexus proceeds with further regrowth and regeneration; and f) endothelial cells are placed in endothelial tubes to provide maintenance and adjustment functions for blood vessels (These cells include pericyte cells in the case of small capillaries, smooth muscle cells in the case of large blood vessels, and cardiac myocytes in the heart).

NRP1 is known to be expressed in a variety of human tumor cell lines and human tumors (such as glioblastoma, astrocytoma, glioma, neuroblastoma, testicular cancer, colorectal cancer, melanoma, pancreatic cancer, lung cancer, breast cancer, esophageal cancer, and prostate cancer). NRP1 is also known to be involved in the effects of proliferation, survival and metastasis of cancer cells of VEGF and semaphorin. Further, it is known that the degree of cancer progression increases or the prognosis of cancer patients is poor according to the degree of NRP1 expression.

When tumors grow, angiogenesis is crucial in the transition from hyperplasia to neoplasia and may play a crucial role in providing nutrients for tumor growth and metastasis. The neovascularization allows the tumor cells to gain growth advantage and proliferative autonomy compared to normal cells. Tumors typically start as single abnormal cells that can proliferate in only few cubic millimeters because of the distance from the available capillary layer and can become stagnant in a "latent" state for extended periods of time without further growth and transmission. Subsequently, some tumor cells are converted into angiogenic phenotypes, activating endothelial cells, and proliferating and maturing into new capillaries. These newly formed blood vessels not only allow the primary tumor to grow continuously, but can also propagate and re-colonize metastatic tumor cells.

In this regard, an anti-NRP1 antibody capable of binding with high affinity to NRP1 and inhibiting the growth of cancer cells is required in order to treat cancers in which NRP1 is overexpressed.

The market for the therapeutic antibody is expected to grow at an average annual rate of 11.8%, reaching $ 89.9 billion in 2017, with cancer treatment being the biggest contributor. Currently, 260 biotechnology companies are developing about 700 therapeutic antibodies of which 220 antibodies are in clinical trials (Gabilondo and Larrick, 2000). Over the past 15 years, a variety of antibodies have been developed, which specially target highly expressed or mutated antigens in cancer cells, and have been administered to patients with blood and solid tumors.

Under these technical backgrounds, the inventors of the present application have sought to develop an antibody for chemotherapy, which is bound to NRP1 known to be expressed in various cancers and is internalized into cells. As a result, the present inventors have developed an anti-NRP1 antibody that is bound to NRP1 with high affinity and is internalized into cells using phage display technology and confirm that such anti-NRP1 antibody can significantly inhibit the movement of cancer cells, thereby completing the present disclosure.

The information described above in the background section is intended to improve only understanding of the background of the present disclosure, and thus the present disclosure may exclude information on a prior art already known to those skilled in the art.

SUMMARY

An object of the present disclosure is to provide a novel antibody binding to NRP1 or an antigen-binding fragment thereof.

Another object of the present disclosure is to provide a nucleic acid encoding the antibody or antigen-binding fragment thereof.

Still another object of the present disclosure is to provide a vector including the nucleic acid, a cell transformed with the vector, and a method for preparing the same.

Yet still another object of the present disclosure is to provide an antibody-drug conjugate including the antibody or antigen-binding fragment thereof.

Yet still another object of the present disclosure is to provide a composition for preventing or treating cancers, including the antibody or the antigen-binding fragment thereof or an antibody-drug conjugate.

In order to achieve the objects as described above, the present disclosure provides the antibody or an antigen-binding fragment thereof to NRP1 (Neuropilin 1), which binds to NRP1 expressed on the cell surface and is internalized into cells.

The present disclosure further provides a nucleic acid encoding a heavy chain variable region of the antibody or antigen-binding fragment thereof.

The present disclosure further provides a vector including the nucleic acid.

The present disclosure further provides a cell transformed with the vector.

The present disclosure further provides a method of producing the antibody or antigen-binding fragment thereof, including the steps of: (a) culturing the cells; and (b) recovering the antibody or antigen-binding fragment thereof from the cultured cells.

The present disclosure further provides an antibody-drug conjugate including said antibody or antigen-binding fragment thereof.

The present disclosure further provides a composition including the antibody or antigen-binding fragment thereof, for preventing or treating cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Unless otherwise defined, all technical and scientific terms used herein have the same meaning as commonly understood by one of ordinary skill in the art to which the present disclosure belongs. In general, the nomenclature used herein is well known and commonly used in the art.

In one aspect, the present disclosure relates to the antibody or antigen-binding fragment thereof to NRP1 (Neuropilin 1), and the antibody or antigen-binding fragment thereof which is bound to NRP1 expressed on the cell surface and is internalized into the cells.

The present inventors have sought to develop an antibody for chemotherapy which is internalized into cells by binding to NRP1 which is known to be expressed in various cancers. As a result, the present inventors have produced anti-NRP1 antibodies that is bound to NRP1 with high affinity and is internalized into cells using phage display technology, and confirmed that such anti-NRP1 antibody can significantly inhibit the migration of cancer cells.

Figure 10A:
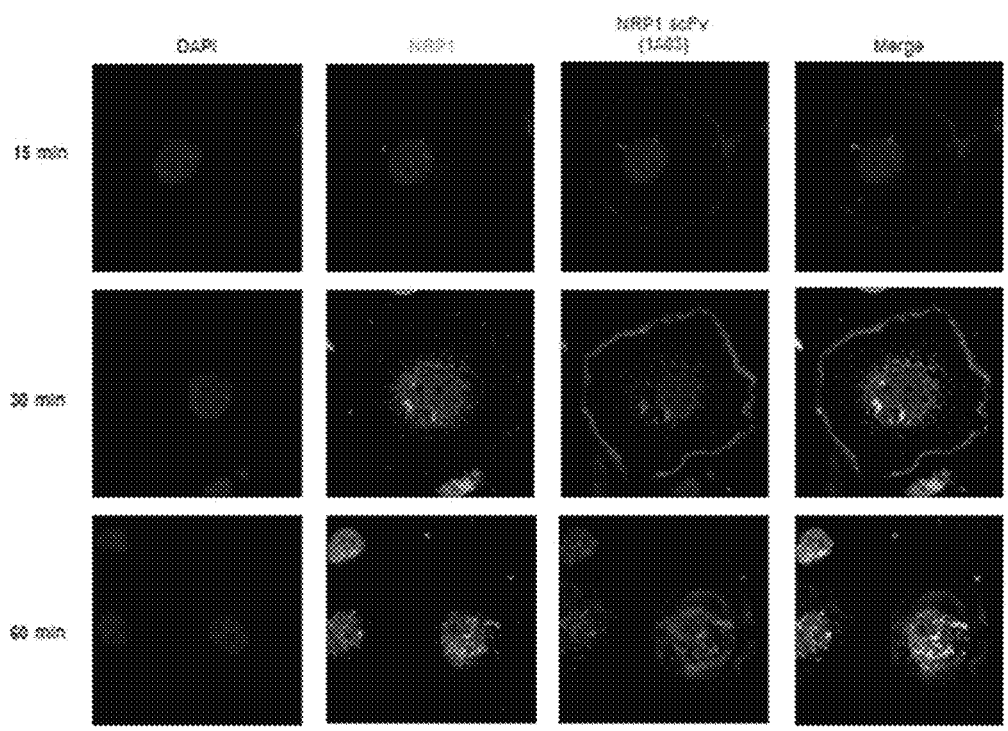
FIGS. 10a to 10c are images obtained by a confocal laser scanning microscope, showing the internalization function of three anti-NRP1 scFv antibodies.
Figure 10B:
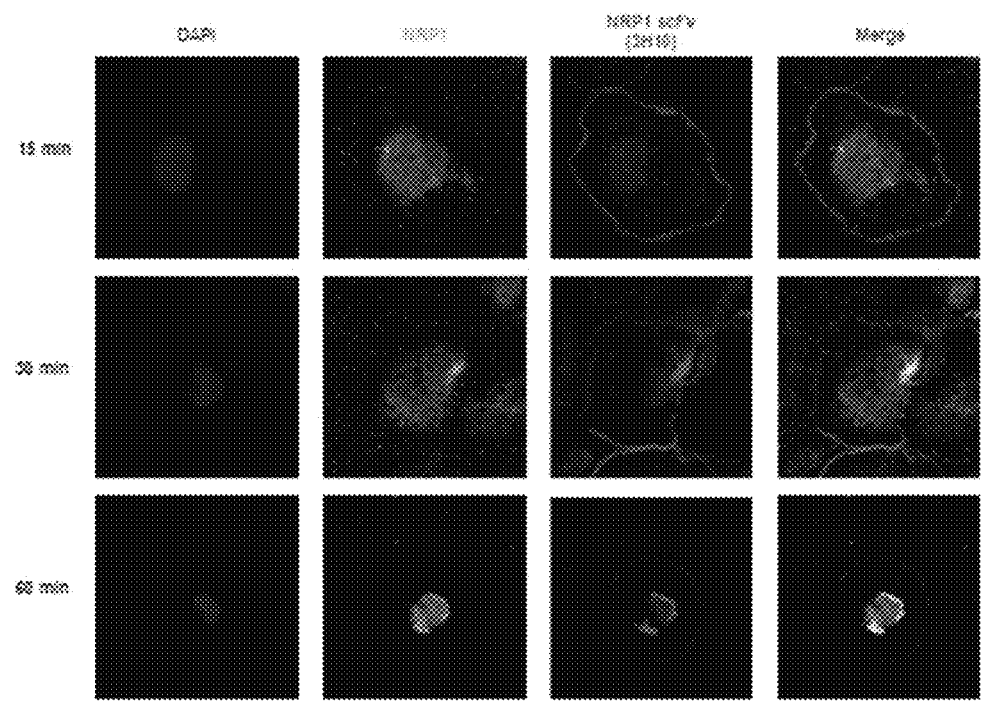
Figure 10C:
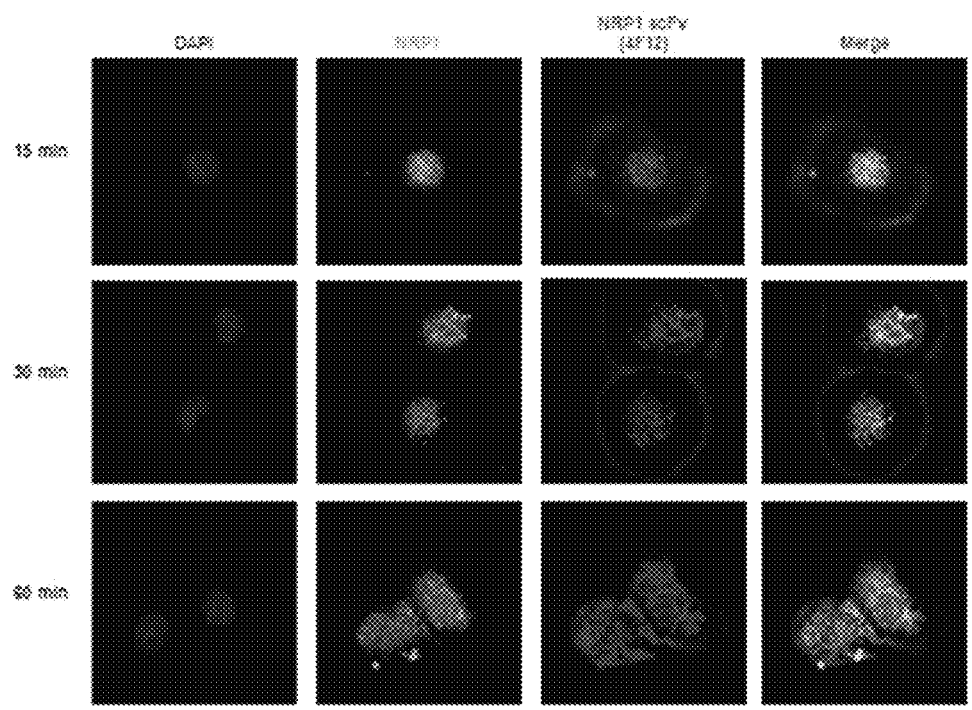

According to an exemplary embodiment of the present disclosure, it has been confirmed that the anti-NRP1 antibody of the present disclosure is bound to NRP1 expressed on the cancer cell surface and is then internalized into the cells (See FIGS. 10a to 10c). Unlike the antibody that is bound to NRP1 on the cell surface and blocks the sub signal transmission at the site, the antibody of the present disclosure is bound to NRP1 of the cell surface and then enters into the cells, so as to block all signal transmissions related to NRP1, thereby expecting huge therapeutic effects.

"Neuropilin" or NRP as used herein collectively includes neuropilin-1 (NRP1), neuropilin-2 (NRP2) and their isoforms and variants. Neuropilin is a 120 to 130 kDa non-tyrosine kinase receptor. There are a number of NRP-1 and NRP-2 splicing variants and soluble isoforms. The basic structure of neurofilin contains five domains: three extracellular domains (a1a2, b1b2 and c), a transmembrane domain, and a cytoplasmic domain. The a1a2 domain is homologous to the complement components Clr and Cls (CUB), which generally contain four cysteine residues forming two disulfide bridges. The b1 b2 domain is homologous to the coagulation factors V and VIII. A central part of the c domain is termed MAM because of its homology with meprin, A5, and the receptor tyrosine phosphatase µ protein. The a1a2 and b1b2 domains are critical for ligand binding whereas the c domain is critical for homo-dimerization or hetero-dimerization.

"Neuropilin-1 mediated biological activity" refers to a physiological or pathological condition in which neuropilin-1 plays a substantial role, for example, but not limited to, exons guidance during embryonic nervous system development or nerve cell regeneration, angiogenesis (including re-angiogenesis), tumorigenesis and tumor metastasis.

The term "antibody" as used herein means an anti-NRP1 antibody that is specifically bound to NRP1. The scope of the present disclosure includes not only the complete antibody form specifically binding to NRP1, but also antigen binding fragments of such antibody molecules.

The complete antibody is a structure having two full-length light chains and two full-length heavy chains, and each light chain is linked by a disulfide bond with a heavy chain. A constant region of the heavy chain has gamma (γ), mu (µ), alpha (α), delta (δ), and epsilon (ε) types. Subclasses have gamma 1 (γ1), gamma 2 (γ2), gamma 3 (γ3), gamma 4 (γ4), alpha 1 (α1), and alpha 2 (α2) types. A constant region of the light chain has kappa (κ) and lambda (λ) types.

An antigen binding fragment or an antibody fragment of an antibody refers to a fragment having an antigen binding function and includes Fab, F(ab'), F(ab')2, Fv, and the like. Fab of the antibody fragments has a structure including variable regions of a light chain and a heavy chain, a constant region of the light chain, and a first constant region (CH1) of the heavy chain with one antigen-binding site. Fab' differs from Fab in that it has a hinge region containing one or more cysteine residues at the C-terminal of the heavy chain CH1 domain The F(ab')2 antibody is produced when the cysteine residue of the hinge region of the Fab' forms a disulfide bond. Recombinant techniques for generating Fv fragments with minimal antibody fragments having only a heavy chain variable region and a light chain variable region are described in PCT International Publication Nos. WO88/10649, WO88/106630, WO88/07085, WO88/07086, and WO88/09344. A two-chain Fv has a non-covalent bonding between a heavy chain variable region and a light chain variable region. A single chain Fv (scFv) is connected to a heavy chain variable region and a light chain variable region via a peptide linker by a covalent bond or directly at the C-terminal. Thus, the single chain Fv (scFv) has a structure such as a dimer like the two-chain Fv. Such an antibody fragment can be obtained using a protein hydrolyzing enzyme (for example, when the whole antibody is cleaved with papain, Fab can be obtained, and when whole antibody is cut with pepsin, F(ab')2 fragment can be obtained), and it can also be produced through gene recombinant technology.

According to an exemplary embodiment of the present disclosure, an antibody is in the form of an Fv (e.g. scFv) or a complete antibody form. Further, the heavy chain constant region can be selected from any one isotype of gamma (γ), mu (µ), alpha (α), delta (δ), and epsilon (ε). For example, the constant region is gamma 1 (IgG1), gamma 3 (IgG3), or gamma 4 (IgG4). The light chain constant region may be kappa or lambda types.

The term "heavy chain" as used herein refers to a full-length heavy chain and fragments thereof including a variable region domain VH including an amino acid sequence with sufficient variable region sequence to confer specificity to an antigen and three constant region domains CH1, CH2, and CH3. The term "light chain" as used herein refers to a full-length heavy chain and fragments thereof including a variable region domain VL including an amino acid sequence with sufficient variable region sequence to confer specificity to an antigen and a constant region domain CL.

The antibody of the present disclosure includes, but are not limited to, a monoclonal antibody, a multi-specific antibody, a human antibody, a humanized antibody, a chimeric antibody, a single chain Fvs (scFV), a single chain antibody, a Fab fragment, a F(ab)' fragment, a disulfide-bond Fvs (sdFV), and an anti-idiotypic (anti-Id) antibody, or epitope-binding fragments of such antibodies, and the like.

The monoclonal antibody refers to an antibody obtained from a substantially homogeneous population of antibodies, i.e., the same except for possible naturally occurring mutations that may be present in trace amounts of individual antibodies that occupy the population. The monoclonal antibody is highly specific and is derived against a single antigenic site.

The non-human (e.g. murine) antibody of the "humanized" form is a chimeric antibody containing minimal sequence derived from non-human immunoglobulin. In most cases, the humanized antibody is a human immunoglobulin (receptor antibody) that has been replaced by a residue from the hypervariable region of a non-human species (donor antibody), such as a mouse, rat, rabbit, and non-human primate, having specificity, affinity, and ability to retain a residue from the hypervariable region of the receptor.

"Human antibody" is a molecule derived from human immunoglobulin and means that all of the amino acid sequences constituting the antibody including the complementarity determining region and the structural region are composed of human immunoglobulin.

A heavy chain and/or light chain is partly identical or homologous to the corresponding sequence in an antibody derived from a particular species or belonging to a particular antibody class or subclass, while the remaining chain(s) are identical or homologous to corresponding sequences in an antibody derived from another species or belonging to another antibody class or subclass "chimeric" antibodies (immunoglobulins) as well as a fragment of such antibody exhibiting the desired biological activity.

"Antibody variable domain" as used herein refers to the light and heavy chain regions of an antibody molecule including the amino acid sequences of a complementarity determining region (CDR; i.e., CDR1, CDR2, and CDR3) and a framework region (FR). VH refers to a variable domain of the heavy chain. VL refers to a variable domain of the light chain.

"Complementarity determining region" (CDR; i.e., CDR1, CDR2, and CDR3) refers to the amino acid residue of the antibody variable domain, which is necessary for antigen binding. Each variable domain typically has three CDR regions identified as CDR1, CDR2, and CDR3.

"Framework region" (FR) is a variable domain residue other than a CDR residue. Each variable domain typically has four FRs identified as FR1, FR2, FR3, and FR4.

According to an exemplary embodiment of the present disclosure, an antibody or antigen-binding fragment thereof includes a heavy chain CDR (complementarity determining region) and light chain CDR as followings: a heavy chain variable region comprising complementarity determining region (CDR) H1 comprising a sequence of SEQ ID NO: 1 or 7, CDRH2 comprising a sequence of SEQ ID NO: 2 or 8, and CDRH3 comprising any one sequence selected from the group consisting of sequences of SEQ ID NOS: 3, 9 and 13;

and a light chain variable region comprising CDRL1 comprising the sequence of SEQ ID NO: 4 or 10, CDRL2 comprising any one sequence selected from the group consisting of sequences of SEQ ID NOS: 5, 11, and 14, and CDRL3 comprising any one sequence selected from the group consisting of sequences of SEQ ID NOS: 6, 12, and 15.

According to an exemplary embodiment of the present disclosure, the antibody or antigen-binding fragment thereof includes a heavy chain variable region and a light chain variable chain having CDR as followings:

(i) a heavy chain variable region comprising CDRH1, CDRH2, and CDRH3, respectively, comprising sequences of SEQ ID NOS: 1 to 3 and a light chain variable region comprising CDRL1, CDRL2, and CDRL3, respectively, comprising sequences of SEQ ID NOS: 4 to 6;

(ii) a heavy chain variable region including CDRH1, CDRH2, and CDRH3, respectively, comprising sequences of SEQ ID NOS: 7 to 9 and a light chain variable region comprising CDRL1, CDRL2, and CDRL3, respectively, comprising sequences of SEQ ID NOS: 10 to 12; or (iii) a heavy chain variable region comprising CDRH1, CDRH2, and CDRH3, respectively, comprising sequences of SEQ ID NOS: 7, 8, and 13 and a light chain variable region comprising CDRL1, CDRL2, and CDRL3, respectively, comprising sequences of SEQ ID NOS: 10, 14, and 15.

According to an exemplary embodiment of the present disclosure, the antibody or antigen-binding fragment thereof may comprise a heavy chain variable region comprising a heavy chain framework region (FR) comprising one sequence selected from the group consisting of sequences of SEQ ID NOS: 28 to 33.

Here, the antibody or antigen-binding fragment thereof may comprise a heavy chain FR1 comprising a sequence of sequence number 28, a heavy chain FR2 comprising a sequence of SEQ ID NO: 29 or 30, a heavy chain FR3 comprising a sequence of SEQ ID NO: 31 or 32, or a heavy chain FR4 comprising a sequence of SEQ ID NO: 33.

Further, the antibody or antigen-binding fragment thereof of the present disclosure may include a light chain variable region including a light chain framework region (FR) comprising one sequence selected from the group consisting of sequences of SEQ ID NOS: 34 to 42.

Here, the antibody or antigen-binding fragment thereof may include a light chain FR1 comprising any one sequence of SEQ ID NOS: 34 to 36, a light chain FR2 comprising any one sequence of SEQ ID NOS: 37 to 39, a light chain FR3 comprising a sequence of SEQ ID NO: 40 or 41, or a light chain FR4 comprising a sequence of SEQ ID NO: 42.

According to an exemplary embodiment of the present disclosure, the antibody or antigen-binding fragment thereof may comprise a heavy chain variable region and a light chain variable chain as followings:

(i) a heavy chain variable region comprising a sequence of SEQ ID NO: 16 and a light chain variable region comprising a sequence of SEQ ID NO: 17; (ii) a heavy chain variable region comprising a sequence of SEQ ID NO: 18 and a light chain variable region comprising a sequence of SEQ ID NO: 19; or (iii) a heavy chain variable region comprising a sequence of SEQ ID NO: 20 and a light chain variable region comprising a sequence of SEQ ID NO: 21.

More specifically, the antibody or antigen-binding fragment thereof of the present disclosure comprises a light chain variable region or a heavy chain variable region as followings:

(i) a heavy chain variable region comprising a sequence of SEQ ID NO: 16 and a light chain variable region comprising a sequence of SEQ ID NO: 17 (4F12 antibody);

(ii) a heavy chain variable region comprising a sequence of SEQ ID NO: 18 and a light chain variable region comprising a sequence of SEQ ID NO: 19 (1A03 antibody); or (iii) a heavy chain variable region comprising a sequence of SEQ ID NO: 20 and a light chain variable region comprising a sequence of SEQ ID NO: 21 (3H10 antibody).

Fv fragment is an antibody fragment containing complete antibody recognition and binding sites. Such region includes a heavy chain variable domain and a light chain variable domain, for example, dimers substantially tightly covalently associated with scFv.

"Fab" fragment contains the variable and constant domains of the light chain and the variable and first constant domain (CH1) of the heavy chain. F(ab')2 antibody fragment generally includes a pair of Fab fragments covalently linked by their hinge cysteine near their carboxy-terminal.

"Single chain Fv" or "scFv" antibody fragment comprises VH and VL domains of the antibody. Such domains are within a single polypeptide chain. The Fv polypeptide may further include a polypeptide linker between the VH domain and the VL domain such that the scFv can form the desired structure for antigen binding.

"Phage display" is a technique for displaying a fusion protein by fusing a mutant polypeptide and at least a part of a coat protein on a surface of phase such as a fibrous phage particle. The phage display is useful for a targeting large library of randomized protein variants to quickly and efficiently classify sequences that bind to target antigens in high affinity. Displaying peptides and protein libraries on phage has been used to screen millions of polypeptides to identify polypeptides with specific binding properties.

The phage display technique has provided a powerful tool for generating and screening novel proteins that bind to specific ligands (e.g., antigens). Using the phage display technique, a large library of protein variants can be generated and sequences binding to the target antigens in high affinity can be quickly classified. The nucleic acid encoding the mutant polypeptide is fused with a nucleic acid sequence encoding a viral coat protein, e.g., a gene III protein or a gene VIII protein. A monovalent phage display system has been developed in which a nucleic acid sequence encoding a protein or polypeptide is fused with a nucleic acid sequence encoding a part of the gene III protein. In the monovalent phage display system, the gene fusion is expressed at a low level, and the wild-type gene III protein is also expressed, thereby maintaining the infectivity of the particles.

Demonstrating the expression of peptides on the fibrous phage surface and the expression of functional antibody fragments in the peripheral cytoplasm of *E. coli* is important in developing antibody phage display libraries. Libraries of antibodies or antigen-binding polypeptides have been prepared in a number of ways, for example by altering a single gene by inserting a random DNA sequence or by cloning a related genic line. The library can be screened for expression of antibodies or antigen binding proteins with the desired characteristics.

The phage display technique has several advantages over conventional hybridomas and recombinant methods for producing antibodies with the desired characteristics. This technique allows the generation of a large antibody library having various sequences in a short time without the use of animals. The production of hybridomas or humanized antibodies may take several months to manufacture. Further, the phage antibody library may produce antibodies against antigens that are toxic or have low antigenicity since no immunity is required. The phage antibody library can also be used to generate and identify novel therapeutic antibodies.

Human antibodies can be generated from virgin B-cell Ig repertoires or human germline sequences non-immunized or immunized using a phage display library. Various lymphatic tissues may be used to prepare virgin or non-immune antigen-binding libraries.

Techniques for identifying and separating high affinity antibodies from a phage display library are important for separating new therapeutic antibodies. The separation of high affinity antibodies from the library may depend on the size of the library, production efficiency in bacterial cells, and library diversity. The size of the library is reduced by inefficient production due to improper folding of an antibody or antigen binding protein and the presence of the stop codon. Expression in bacterial cells can be inhibited when an antibody or antigen binding domain is not properly folded. The expression can be increased by alternately mutating residues on a surface of a variable/constant interface or selected CDR residues. A sequence of the framework region is one element to provide appropriate folding when antibody phage libraries are generated in bacterial cells.

It is important to generate various libraries of an antibody or antigen binding proteins in high affinity antibody separation. The CDR3 region has been found to often participate in antigen binding. The CDR3 region on a heavy chain varies considerably in terms of size, sequence, and structural steric conformation so that various libraries can be prepared using the CDR3 region.

Further, diversity may be generated by randomizing the CDR regions of the variable heavy and light chains using all 20 amino acids at each position. The use of all 20 amino acids results in an increased variability of variant antibody sequences and an increased chance of identifying new antibodies.

An antibody or antibody fragment of the present disclosure may include, within the scope of specifically recognizing NRP1, the sequence of the anti-NRP1 antibody of the present disclosure described herein as well as biological equivalents thereof. The amino acid sequence of the antibody may be additionally modified to further improve the binding affinity and/or other biological properties of the antibody. Such modifications include, for example, deletion, insertion and/or substitution of the amino acid sequence residues of the antibody. Such amino acid variations are made based on the relative similarity of amino acid side chain substituents, such as hydrophobicity, hydrophilicity, charge, and size. By analysis of the size, shape and type of amino acid side chain substituents, it is recognized that each of arginine, lysine and histidine is a positively charged residue; alanine, glycine and serine have similar sizes; and phenylalanine, tryptophan and tyrosine have similar shapes. Based on these considerations, it is thus found that arginine, lysine and histidine; alanine, glycine and serine; and phenylalanine, tryptophan and tyrosine, respectively, are biologically functional equivalents.

On introduction of mutations, the hydropathic index of amino acids can be considered. Each amino acid is assigned a hydrophobic index according to its hydrophobicity and charge: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydrophobic amino acid index is very important in imparting the interactive biological function of proteins. It is well known that substitution with an amino acid having a similar hydrophobic index can retain similar biological activities. When a mutation is introduced with reference to a hydrophobic index, the substitution is made between amino acids showing a hydrophobic index difference preferably within ±2, more preferably within ±1, even more preferably within ±0.5.

Meanwhile, it is also well known that the substitution between amino acids with similar hydrophilicity values leads to proteins with equivalent biological activity. As disclosed in U.S. Pat. No. 4,554,101, the following hydrophilicity values are assigned to each amino acid residue: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

Amino acid substitution in proteins that do not totally alter the activity of the molecule is known in the art (H. Neurath, R. L. Hill, The Proteins, Academic Press, New York, 1979). The substitution occurs the most commonly between amino acid residues, e.g., Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly.

Considering the mutation having the above-mentioned biological equivalent activity, the antibody of the present disclosure or the nucleic acid molecule encoding the same is interpreted to include a sequence showing substantial identity with the sequence described in sequence lists. The substantial identity means a sequence showing at least 61% homology, more preferably 70% homology, even more preferably 80% homology, and most preferably 90% homology by aligning the sequence of the present disclosure with any other sequence as much as possible and analyzing the aligned sequence using algorithms commonly used in the art. Alignment methods for sequence comparison are well known in the art. NCBI Basic Local Alignment Search Tool (BLAST) may be accessible from, e.g., NBCI and can be used in association with sequence analysis programs such as blastp, blasm, blastx, tblastn and tblastx on the Internet. BLSAT is available at www.ncbi.nlm nih.gov/BLAST/. A comparison of sequence homology using this program can be found at www.ncbi.nlm.nih.gov/BLAST/blast_help.html.

In another aspect, the present disclosure relates to a nucleic acid encoding the antibody or antigen-binding fragment thereof.

The antibody or antigen-binding fragment thereof of the present disclosure may be recombinantly produced by isolating the nucleic acid encoding an antibody or antigen-binding fragment thereof of the present disclosure. The nucleic acid is isolated and inserted into a cloneable vector to result in further cloning (amplification of DNA) or further expression. Based on this, the present disclosure relates to a vector including the nucleic acid according to another aspect of the present disclosure.

"Nucleic acid" has a broad meaning including DNA (gDNA and cDNA) and RNA molecules. Nucleotides, basic elements of nucleic acids, include natural nucleotides as well as analogues in which sugar or base sites are modified. The sequence of the nucleic acid encoding the heavy and light chain variable regions of the present disclosure may be modified. Such modifications include the addition, deletion, or non-conservative substitution or conservative substitution of nucleotides.

According to an exemplary embodiment of the present disclosure, the nucleic acid encoding the heavy chain variable region of the antibody or antigen binding portion thereof may comprise sequence of SEQ ID NO: 22, 24 or 26, and the nucleic acid encoding the light chain variable region may comprise sequence of SEQ ID NO: 23, 25 or 27.

The nucleic acid of the present disclosure is interpreted to include a nucleotide sequence that exhibits substantial identity to the nucleotide sequence. The substantial identity means a nucleotide sequence showing at least 80% homology, more preferably at least 90% homology, and most preferably at least 95% homology by aligning the nucleotide sequence of the present disclosure with any other sequence as much as possible and analyzing the aligned sequence using algorithms commonly used in the art.

The DNA encoding the antibody can be easily separated or synthesized using conventional procedures (for example, using an oligonucleotide probe capable of specifically binding to DNA encoding the heavy chain and the light chain of the antibody). Many vectors are available. Vector components generally include, but are not limited to, one or more of the following: a signal sequence, a origin of replication, one or more marker gene, an enhancer element, a promoter, and a transcription termination sequence.

The term "vector" as used herein, includes a plasmid vector; a cosmid vector; a bacteriophage vector; and a viral vector, e.g., an adenovirus vector, retroviral vectors, and adeno-associated viral vectors as a mean for expressing a target gene in a host cell. The nucleic acid encoding the antibody in the vector is operably linked to a promoter.

"operably linked" is meant a functional linkage between a nucleic acid expression control sequence (e.g., an array of promoter, signal sequence, or transcription regulation factor binding site) and another nucleic acid sequence, thereby controlling the transcription and/or translation of another nucleic acid sequence.

When a prokaryotic cell is used as a host, a strong promoter capable of promoting transcription (such as a tac promoter, lac promoter, lacUV5 promoter, lpp promoter, pLλ promoter, pRλ promoter, rac5 promoter, amp promoter, recA promoter, SP6 promoter, trp promoter, and T7 promoter), a ribosome binding site for initiation of translation, and a transcription/translation termination sequence are generally included. Further, for example, when a eukaryotic cell is used as a host, a promoter derived from a genome of a mammalian cell (e.g., a metallothionein promoter, a β-actin promoter, a human hemoglobin promoter and a human muscle creatine promoter) or a promoter derived from an mammalian virus (e.g., adenovirus late promoter, vaccinia virus 7.5 K promoter, SV40 promoter, cytomegalovirus (CMV) promoter, HSV tk promoter, mouse mammary tumor virus (MMTV) promoter, HIV LTR promoter, epstein barr virus (EBV) promoter of moloney virus and Rous sarcoma virus (RSV) promoter) can be used, and generally have a polyadenylation sequence as a transcription termination sequence.

Optionally, the vector may be fused with another sequence in order to facilitate purification of an antibody expressed therefrom. Fused sequences include, for example, glutathione S-transferase (Pharmacia, USA), maltose binding protein (NEB, USA), FLAG (IBI, USA), and 6× His (hexahistidine; Quiagen, USA).

The vector includes an antibiotic resistance gene commonly used in the art as selectable markers, and the resistance gene includes, for example, the genes for ampicillin, gentamycin, carbenicillin, chloramphenicol, streptomycin, kanamycin, geneticin, neomycin and, tetracycline.

According to another aspect of the present disclosure, there is provided a cell transformed with the above-mentioned vector. The cell used to produce the antibody of the present disclosure may be, but is not limited to, a prokaryote, yeast, or higher eukaryotic cell.

The prokaryotic host cell can be used, for example, a strain belonging to the genus Bacillus such as *Escherichia coli*, *Bacillus subtilis*, and *Bacillus thuringiensis*, *Streptomyces*, *Pseudomonas* (for example, *Pseudomonas putida*), *Proteus mirabilis*, and *Staphylococcus* (for example, *Staphylococcus carnosus*).

Meanwhile, interest in animal cells is greatest, and an example of a useful host cell line may be, but is not limited thereto, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U205, or HT1080.

According to another aspect of the present disclosure, there is provided a method of producing the antibody or antigen-binding fragment thereof, comprising: (a) culturing the cells; and (b) recovering the antibody or antigen-binding fragment thereof from the cultured cells. The cells can be cultured in various media. Commercially available media can be used as a culture medium without limitation. All other essential supplements known to those skilled in the art may be included in the appropriate concentrations. Culturing conditions, e.g., temperature and pH have already been used with the selected host cells for expression, which will be apparent to those skilled in the art.

When the antibody or antigen-binding fragment thereof is recovered, impurities can be removed, e.g., by centrifugation or ultrafiltration, and the resultant can be purified, for example, by affinity chromatography. Additional purification techniques may be used, such as anion or cation exchange chromatography, hydrophobic interaction chromatography, and hydroxyl apatite chromatography.

According to another aspect of the present disclosure, there is provided an antibody-drug conjugate comprising the antibody or antigen-binding fragment thereof and a drug. Since NRP1 is a molecule that is overexpressed on a surface of a cancer cell, when the antibody-drug conjugate in which a drug is additionally bound to the antibody of the present disclosure is used, it is possible to selectively target only the cancer cell while minimally affecting normal cells.

Such drugs include chemicals, radionuclides, immunotherapeutic agents, cytokines, chemokines, toxins, biologic agents and enzyme inhibitors. For example, the antibody or fragment thereof of the present disclosure may be directly or indirectly bound to an anti-cancer agent, e.g., acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol, beta-2-deoxythioguanosine, bisantrene HCl, bleomycin sulfate, busulfan, buthionine sulfoximine, BWA 773U82, BW 502U83/HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, corynebacterium parvum, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydro galactitol, diaziquone, dibromodulcitol, didemnin B, ethyldithiocarbamate, diglycoaldehyde, dihydro-5-azacytine, doxorubicin, echinomycin, dedatrexate, edelfosine, eplolnitin, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5'-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, 4-ipomeanole, iproplatin, isotretinoin, leucovorin calcium, leuprolide acetate, levamisole, liposome daunorubicin, liposome encapsulated doxorubicin, lomustine, lonidamine, maytansine, mechlorethamine hydrochloride, melphalan, menogaril, merbarone, 6-mercaptopurine, mesna, methanol extract of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor (TNF), uracil mustard, vinblastine sulfate, vincristine sulfate, vindesine, vinorelbine, vinzolidine, Yoshi 864, zorubicin, cytosine arabinoside, etoposide, melphalan, taxotele, and taxol.

According to another aspect of the present disclosure, there is provided a composition for preventing or treating a cancer, comprising the antibody or antigen-binding fragment thereof or the antibody-drug conjugate as an active ingredient.

The present disclosure may be, e.g., a pharmaceutical composition for preventing or treating a cancer, comprising (a) a pharmaceutical effective amount of the antibody or an antigen-binding fragment thereof, or the antibody-drug conjugate binding to NRP1 according to the present disclosure and (b) a pharmaceutically acceptable carrier. The present disclosure also relates to a method for prevention or treatment of a cancer, comprising administering an effective amount of the antibody or an antigen-binding fragment thereof, or the antibody-drug conjugate binding to NRP1 according to the present disclosure to a patient.

Since the anti-NRP1 antibody or antigen-binding fragment thereof of the present disclosure is used as an active ingredient, the descriptions common to both of them are excluded in order to avoid the excessive complexity of the present specification caused by the repeated descriptions.

As demonstrated in Examples as described below, the anti-NRP1 antibodies according to the present disclosure can inhibit the migration of cancer cells expressing NRP1 (see FIG. 11). Thus, the antibody or antigen-binding fragment thereof of the present disclosure binds to NRP1 with high affinity and thus inhibits the movement of cancer cells overexpressing NRP1, so that it can be used in the form of an antibody alone or an antibody-drug conjugate in the prevention and treatment of a cancer.

"Prevention" means any action that inhibits or delays progress of a cancer by administration of a composition according to the present disclosure, and "treatment" means suppression of development, alleviation, or elimination of a cancer.

The composition is applied to a disease that is a cancer overexpressing NRP1, for examples, glioblastoma, astrocytoma, glioma, neuroblastoma, testicular cancer, colon cancer, melanoma, pancreatic cancer, lung cancer, breast cancer, esophageal cancer, and prostate cancer.

"Cancer overexpressing NRP1" refers to a cancer having NRP1 on the cancer cell surface at a significantly higher level compared to non-cancerous cells of the same tissue type.

According to an exemplary embodiment of present disclosure, a composition is for inhibiting the metastasis or invasion of cancer cells. The present disclosure also relates to a method for inhibiting the metastasis or invasion of cancer cells by treating an antibody binding to NRP1 or an antigen-binding fragment thereof, or an antibody-drug conjugate according to the present disclosure. A pharmaceutically acceptable carrier to be contained in the composition of the present disclosure is conventionally used in the formulation and includes, but are not limited to, lactose, dextrose, sucrose, sorbitol, mannitol, starch, acacia rubber, calcium phosphate, alginate, gelatin, calcium silicate, microcrystalline cellulose, polyvinylpyrrolidone, water, syrup, methylcellulose, methylhydroxybenzoate, propylhydroxybenzoate, talc, magnesium stearate, mineral oil, and the like. The composition of the present disclosure may further include, e.g., a lubricant, a wetting agent, a sweetener, a flavoring agent, an emulsifying agent, a suspending agent, and a preservative in addition to the component.

The pharmaceutical composition of the present disclosure may be administered orally or parenterally. The parenteral administration is carried out by intravenous injection, subcutaneous injection, intramuscular injection, intraperitoneal injection, endothelial administration, topical administration, intranasal administration, intrapulmonary administration, rectal administration, and the like.

Since the protein or peptide is digested when administered orally, the oral composition should be formulated or active drug agents should be coated in order to protect decomposition thereof in a stomach. Further, the pharmaceutical composition may be administered by any device capable of transferring the active substance to the target cell.

The appropriate dosage of the composition according to the present disclosure may vary depending on factors such as the formulation method, the administration method, patient's age, body weight, sex, pathological condition, food, administration time, route of administration, excretion rate and responsiveness. Thus, a commonly skilled physician can easily determine and prescribe a dosage that is effective for the desired treatment or prophylaxis. For example, the daily dosage of the pharmaceutical composition of the present disclosure is 0.0001 mg/kg to 100 mg/kg. The term "pharmaceutically effective amount" as used herein refers to an amount sufficient to prevent or treat a cancer.

The pharmaceutical composition of the present disclosure may be formulated using a pharmaceutically acceptable carrier and/or an excipient according to a method which can be easily carried out by those having ordinary skill in the art to which the present disclosure belongs to be produced in a unit dosage form or into a multi-dose container. Here, the formulations may be in the form of solutions, suspensions or emulsions in oils or aqueous media, or in the form of extracts, grains, suppositories, powders, granules, tablets or capsules, and may additionally include dispersing or stabilizing agents.

The composition of the present disclosure may be administered as an individual therapeutic agent or in combination with another therapeutic agent, and may be administered sequentially or simultaneously with a conventional therapeutic agent.

EXAMPLES

Hereinafter, the present disclosure will be described in more detail with reference to examples. The examples are for only descriptive purposes, and it will be understood by those skilled in the art that the scope of the present disclosure is not construed as being limited to the examples.

Example 1

Antibody Internalization Identification Using Patient-Derived Cells

Figure 1:
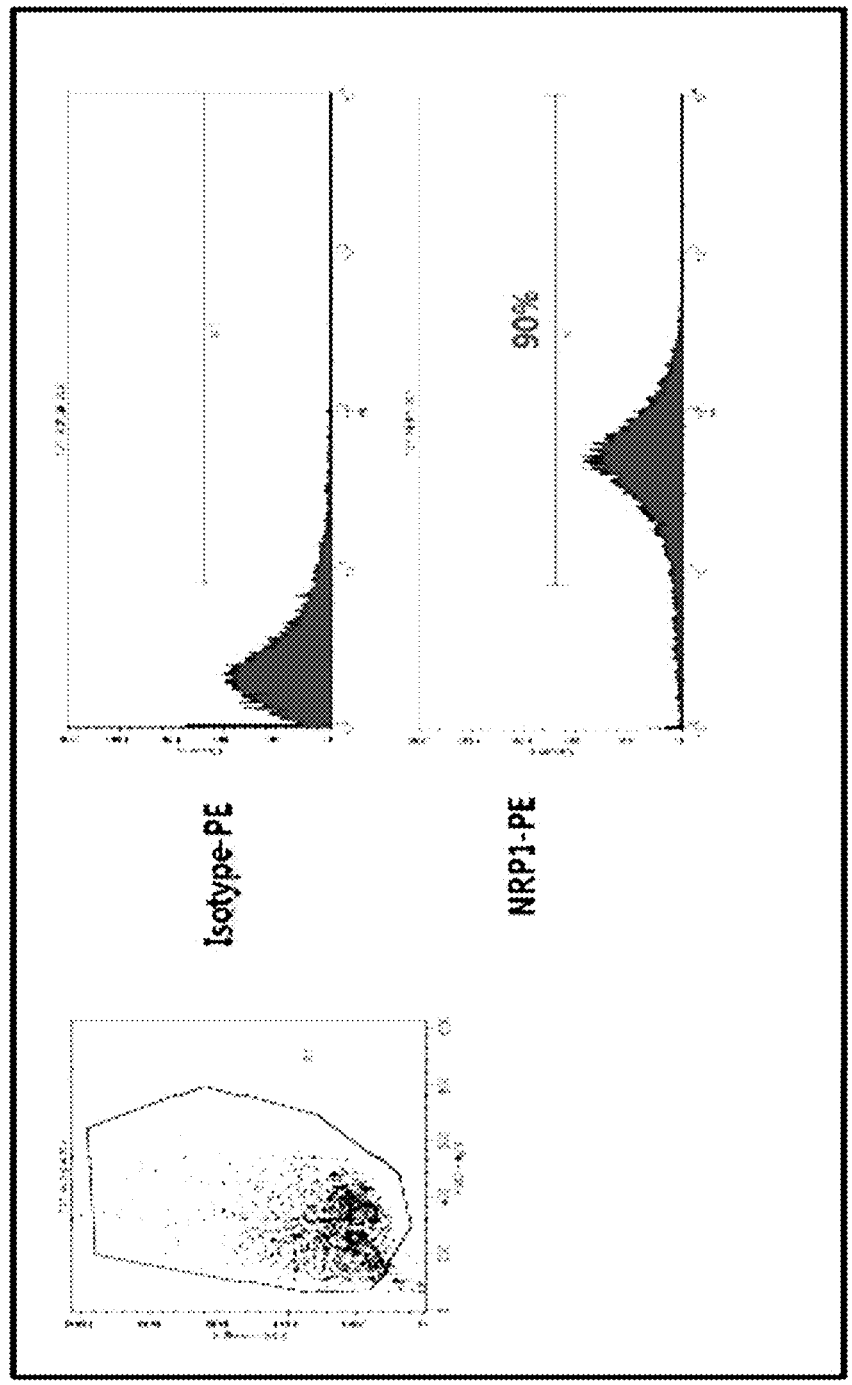
FIG. 1 shows FACS analysis results of patient-derived cells overexpressing NRP1.

Among the patient-derived cells possessed by the project team (Institute for refractory cancer research, Samsung medical center) in order to screen cells required for cell panning for identification of anti-NRP1 antibody fragments, cells with high expression level of NRP1 were selected with fluorescence activated cell sorting (FACS) method. Among them, patient-derived cells obtained from Institute for Refractory Cancer Research at Samsung Medical Center, in which NRP1 was expressed on the surface thereof with the highest expression level, were used for cell panning. The results of FACS analysis of patient-derived cells are shown in FIG. 1.

The scFv antibody fragments that bind to human NRP1 were identified by phage display screening using the previously prepared synthetic scFv antibody fragment phage library (Yang et al., Mol. Cells. 27: 225-235, 2009). Four sub-library samples each was cultured in 400 ml culture medium (SB/ampicillin/2% glucose) for two hours to recover the phagemid vector introduced into *Escherichia coli* host cell ER2537 in a phage form. When the absorbance is about 0.5 to about 0.7 at optical density (OD) 600, the supernatant was removed by centrifugation at 5000 g for 20 minutes, and then suspended in 400 ml of a secondary culture medium (SB/ampicillin). Then, $10^{12}$ pfu (plaque forming unit) of a helper phage (VCSM13) was added and cultured for one hour. Next, 70 µg/ml of kanamycin antibiotic (an antibiotic gene introduced in helper phage) was added and cultured overnight at 30° C. to allow the phage library to be eliminated outside the host cell. Then, the culture obtained by centrifugation was precipitated only in the form of phage using polyethylene glycol (PEG) solution to obtain a phage library.

The obtained phage library and patient-derived cells ($4 \times 10^6$) which are patient-derived cells with high NRP1 expression were mixed to be placed in a total of 5 ml of NBA (neurobasal medium), fixed in a rotator at 4° C., and then rotated 360 degrees for one hour to two hours. Then, the cells were centrifuged at 300 g for 5 minutes to remove the phage particles that did not bind to the patient-derived cells, and then the cells were washed again by adding 5 ml of NBA. This procedure was repeated four times. In the final step, patient-derived cells and phage were placed in a T flask using 5 ml of NBA placed in an incubator having 37° C. and incubated for 30 minutes at 37° C. to allow the phage particles attached to the cell surface to pass through the cells.

Figure 2:
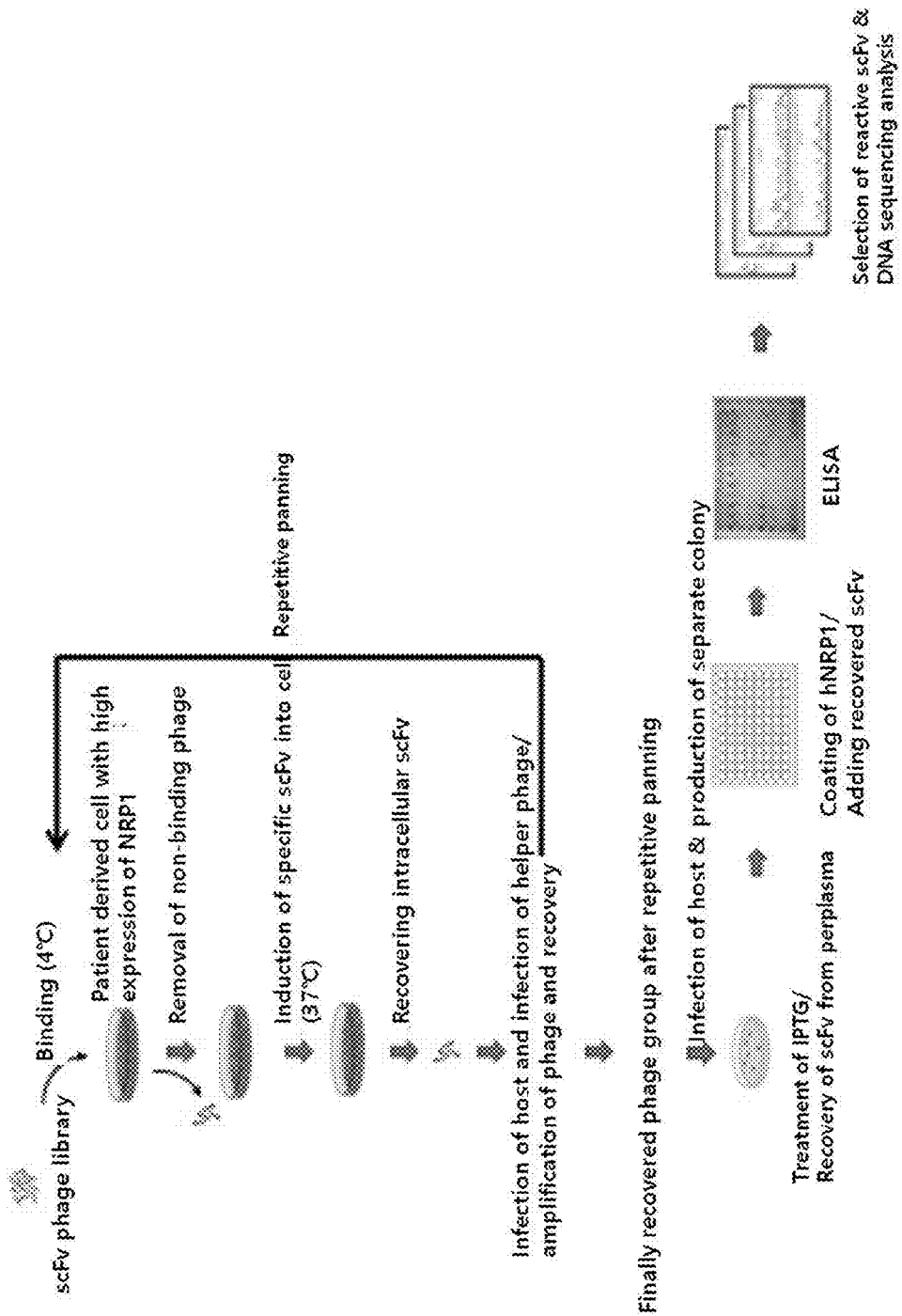
FIG. 2 shows the results of phage display screening for identification of anti-NRP1 scFv antibody fragments.

Then, the cells were placed in a 15-ml conical tube, centrifuged at 300 g for 5 minutes to separate the cells, and then washed with 5 ml of cold PBS (phosphate buffered saline). The washing process was repeated 6 times. The frequency of this process is increased as the number of the cell panning increases. Then, 5 ml of 0.1 M glycine (pH 2.2) was added, and the mixture was kept at room temperature for 5 minutes to separate the cell surface-attached phage particles from the cell surface. Then, the cells were centrifuged at 300 g for 5 minutes to separate only the cells, and 0.5 ml of 100 mM TEA was added. The cells were transferred to an e-tube and left at room temperature for 15 minutes. Next, the cell debris was separated by centrifugation at 12,000 rpm for 5 minutes, and the supernatant containing the phage particles in the cells was neutralized by mixing with 1 ml of 2M Tris (pH 8). Thereafter, the cells were placed in 8.5 ml of a culture medium (SB) containing the pre-incubated ER2537, and cultured at 37° C. at 120 rpm to infect *Escherichia coli* host cell ER2537. Thereafter, ER2537 submerged by centrifugation at 3,000 rpm for 15 minutes was mixed with 500 µg of a culture medium (SB), followed by spreading on a 15 cm culture medium. After culturing, 5 ml of SB culture medium (50% glycerol) was added to recover and store colonies (−80° C.). To proceed with repeated cell panning, 1 ml of the stored prior phage solution was selected and subjected to phage particle amplification. After incubation in host cell ER2537, the helper phage was added to separate the recovered phage particles by PEG precipitation. Those were used for the next round of panning in the same scheme. The third round of panning was performed, and the cell panning procedure is shown in FIG. 2. It was confirmed that the proportion of the phage particles after the panning compared to the pre-panning was increased as the number of repetitions increased. This means that the internalized phage particles were amplified through cell panning, and the results are shown in Table 1.

TABLE 1

| Cell panning using patient-derived cells | | | | |
|---|---|---|---|---|
| | input | wash | output | Output/input |
| 1 round | $1.1 * 10^{13}$ | $2.2 * 10^4$ | $2.7 * 10^3$ | $2.5/10^{10}$ |
| 2 round | $2.5 * 10^{13}$ | $5.0 * 10^3$ | $1.32 * 10^5$ | $5.28/10^9$ |
| 3 round | $1.5 * 10^{12}$ | $3.1 * 10^4$ | $1.49 * 10^6$ | $9.93/10^7$ |

Example 2

ELISA and Sequencing Analysis for Anti-NRP1 scFv Candidate's Selection

The phage particles recovered from the 3rd round cell panning were confirmed as colonies in the culture medium through host cell (ER2537) infection. These colonies were selected to be inoculated in 96-well plates containing 200 µl of SB/ampicillin culture medium and then incubated for 2 hours to 3 hours at 37° C.

Then, each well was treated with IPTG (Isopropyl beta-D-1-thiogalactopyranoside) at a final concentration of 1 mM for induction of scFv-pIII protein expression and cultured overnight at 30° C. The cultured plate was centrifuged at 3,000 rpm for 15 minutes to remove the supernatant. Thereafter, in order to recover the phage particles in the periplasm of the cultured cells, 40 µl of TES solution (20% w/v sucrose, 50 mM Tris, 1 mM EDTA, pH 8.0) was put in each well and left at 4° C. for 30 minutes so as to dissolve the cells. Then, the cells were treated with 60 μl of 0.2×TES solution and incubated at 4° C. for 30 minutes to decompose the cells with osmotic pressure. Then, the plate was centrifuged at 3,000 rpm for 15 minutes to obtain supernatant scFv-pIII protein.

25 μl of the obtained supernatant was added in each of a 96-well plate coated with human NRP1 protein prepared in advance, followed by binding at room temperature for 1 hour, and followed by washing with TBST and distilled water six times. Then, the resultant products were bound to HRP-conjugated anti-HA antibody capable of binding to the HA tag of scFv-pIII for 1 hour at room temperature and then washed six times with TBST (0.1% Tween 20) and distilled water. TMB solution was used to induce the color reaction. The color reaction was stopped with $H_2SO_4$ solution, and its value was measured at 450 nm of OD.

Figure 3:
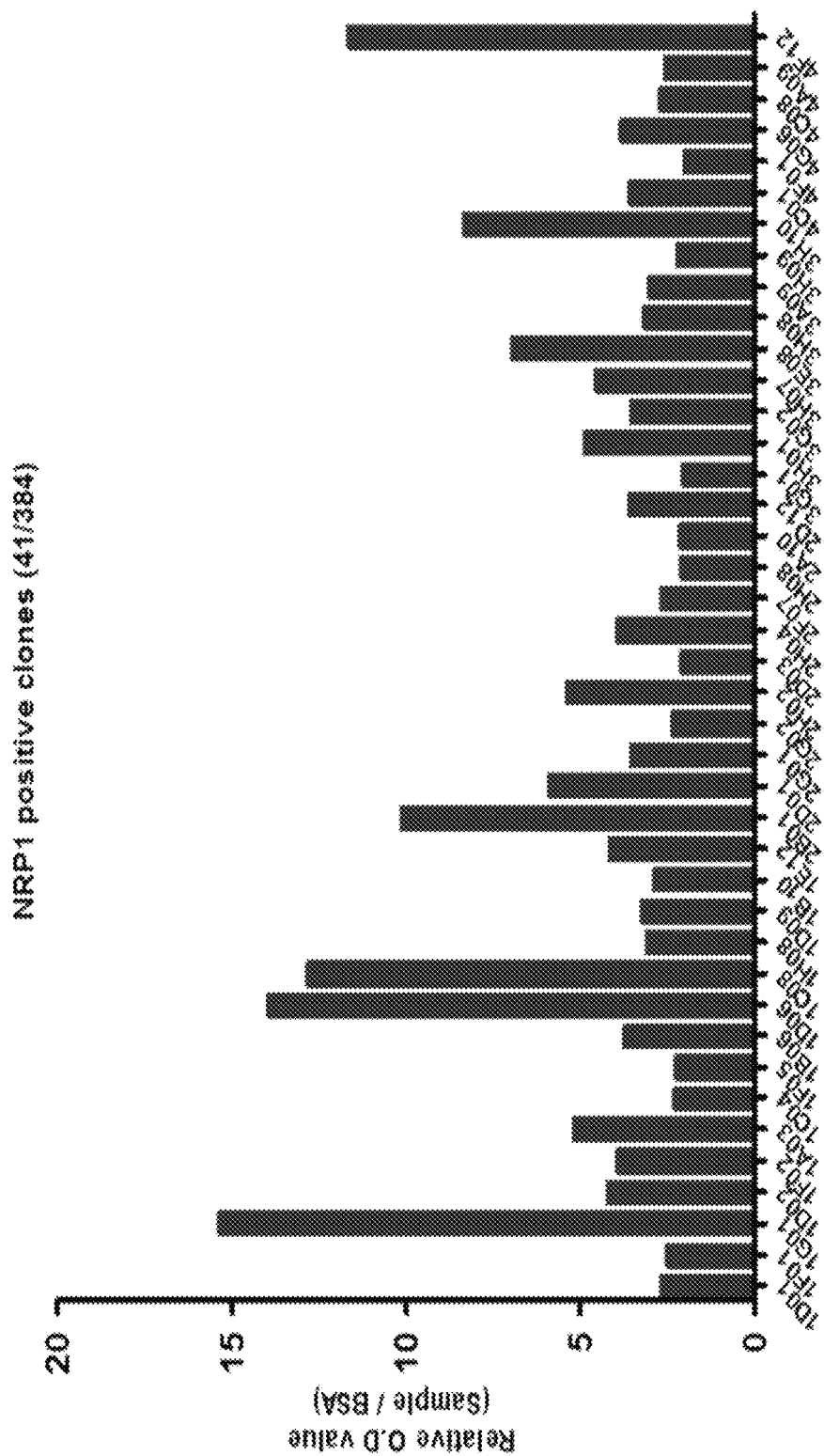
FIG. 3 shows the binding affinity of 41 kinds of scFv antibody fragments binding to human NRP1.

The total number of clones analyzed was 384, of which 41 clones (binding potency>2) showed high binding ability to human NRP1 (See FIG. 3). As a control, BSA solution was used. 10 clones with high binding ability were selected by ELISA among these 41 clones. Then, the phagemid was recovered from 10 clones, and DNA sequencing was performed, and clones having a total of 6 different sequences were selected. Clones with different sequences were selected except 3H10, which is the same sequence as 1C08, and finally 3H10, 1A03 and 4F12 clones were selected as anti-NRP1 scFv candidates. The amino acid sequences of the 3H10, 1A03 and 4F12 clones are shown in Table 2.

TABLE 2

| Sequences of Heavy Chain FR/CDR of anti-NRP1 scFv | | | | | | | |
|---|---|---|---|---|---|---|---|
| | FR1 | CDR1 | FR2 | CDR2 | FR3 | CDR3 | FR4 |
| 1A03 | EVQLLE SGGGL VQPGG SLRL SCAAS (SEQ ID NO: 28) | GFTFSSYY (SEQ ID NO: 7) | MSWV RQA PGKGL EWVSA (SEQ ID NO: 29) | ISPGSSNK (SEQ ID NO: 8) | YYADSVQG RFTISRDNSK NTLYLQMN SLRAEDTAV YYC (SEQ ID NO: 31) | ARRK KSFDY (SEQ ID NO: 9) | WGQGT LVTVSS (SEQ ID NO: 33) |
| 3H10 | EVQLLE SGGGL VQPGG SLRL SCAAS (SEQ ID NO: 28) | GFTFSSYY (SEQ ID NO: 7) | MSWV RQA PGKGL EWVSA (SEQ ID NO: 29) | ISPGSSNK (SEQ ID NO: 8) | YYADSVKG RFTISRDNSK NTLYLQMN SLRAEDTAV YYC (SEQ ID NO: 32) | ARRK YMFDY (SEQ ID NO: 13) | WGQGT LVTVSS (SEQ ID NO: 33) |
| 4F12 | EVQLLE SGGGL VQPGG SLRL SCAAS (SEQ ID NO: 28) | GFTFSGYA (SEQ ID NO: 1) | MSWV RQA PGKGL EWVSG (SEQ ID NO: 30) | ISPGSGST (SEQ ID NO: 2) | YYADSVKG RFTISRDNSK NTLYLQMN SLRAEDTAV YYC (SEQ ID NO: 32) | AKRK TRFDY (SEQ ID NO: 3) | WGQGT LVTVSS (SEQ ID NO: 33) |

| Sequences of Light Chain FR/CDR of anti-NRP1 scFv | | | | | | | |
|---|---|---|---|---|---|---|---|
| | FR1 | CDR1 | FR2 | CDR2 | FR3 | CDR3 | FR4 |
| 1A03 | QSVLT QPPSAS GTPGQ RVTI SCSGP (SEQ ID NO: 34) | SSNIGNND (SEQ ID NO: 10) | VSWY QQL PGTAP KLLIY (SEQ ID NO: 37) | SDN | NRPSGVP DRFSGSKS GTSASLAIS GLR SEDEADYYC (SEQ ID NO: 40) | GAWVA SLSAYV (SEQ ID NO: 12) | FGGGT KLTVL (SEQ ID NO: 42) |
| 3H10 | QSVLT QPPSAS GTPGQ RVTI SCTGS (SEQ ID NO: 35) | SSNIGNND (SEQ ID NO: 10) | VYWY QQL PGTAP KLLIY (SEQ ID NO: 38) | SDS | NRPSGVP DRFSGSKS GTSASLAIS GLR SEDEADYYC (SEQ ID NO: 40) | ASWDS SLSGYV (SEQ ID NO: 15) | FGGGT KLTVL (SEQ ID NO: 42) |
| 4F12 | QSVLT QPPSAS GTPGR RVTI SCSGS (SEQ ID NO: 34) | SSNIGNNS (SEQ ID NO: 4) | VYWY QQL PGTAP KLLIY (SEQ ID NO: 39) | ANN | KRPSGVP DRFSGSKS GTSASLAIS GLR SEDEADYYC (SEQ ID NO: 41) | AAWDS SLNGYV (SEQ ID NO: 6) | FGGGT KLTVL (SEQ ID NO: 42) |

Example 3

Production of Anti-NRP1 scFv and Confirmation of NRP1 Binding Ability

Figure 4:
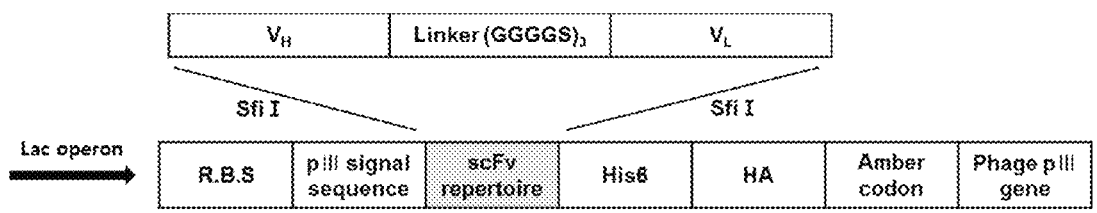
FIG. 4 is a schematic diagram of a phagemid vector for the production of a scFv antibody fragment.
Figure 5:
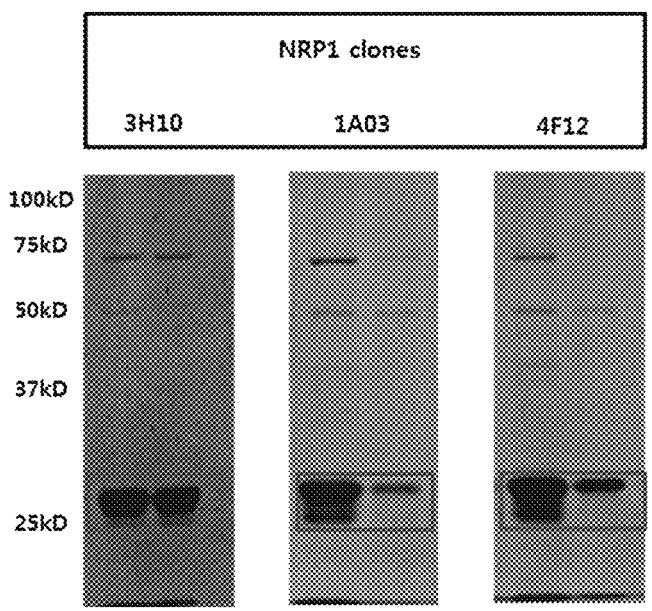
FIG. 5 shows the results of Coomassie staining of each purified scFv antibody fragment.

The basic structure of phagemid is shown in FIG. 4. In the case of the host cell ER2537 used in the above examples, scFv cannot be alone expressed because it inhibits the transcriptional suppression codon (amber codon (UAG)) located in front of phage pIII. Therefore, the phagemid was transfected into the expression strain using an expression strain (TOP10F') which is a non-suppressor strain. Thereafter, DNA sequence analysis revealed that each phagemid was expressed without expression of the mutant. The expression strain was taken as a colony, inoculated into 3 ml of LB/ampicillin culture medium, and cultured overnight at 37° C. Thereafter, 3 ml of the overnight culture was transferred to a 400 ml culture medium (SB/ampicillin) and cultured at OD 600 until the concentration reached 0.5 to 0.7. A final concentration of 1 mM IPTG was added and cultured overnight at 30° C. After the culture was centrifuged, 40 ml of TES solution was used to dissolve the expression host, and then 60 ml of 0.2×TES was added to recover the phage particles in a periplasm. The recovered supernatant was filtered through a 0.45 μm filter. For His-tag purification, the scFv protein presented in the filtered solution was added to 1 ml of Ni-NTA bead (Qiagen) and bound for 1 hour at room temperature. Thereafter, the result was packed in a gravity column (Bio-rad) and recovered via 200 mM imidazole solution. After the expression and purification of each clone, it was confirmed that a size of scFv was about 28 kDa by SDS-PAGE and coomassie blue staining (See FIG. 5).

ELISA was performed using the purified scFv to confirm the presence of binding ability to the target NRP1. In 96 wells coated with 200 ng of NRP1 protein and 96 wells coated with 200 ng of BSA as a control group, they were bound at a concentration of 5 μg/ml per each clone for 1 hour by ELISA (3 times repetition) at a room temperature. Thereafter, the results were washed three times with 0.1% TB ST, treated with HRP-conjugated HA antibody for 1 hour, washed again, and then left with TMB solution for 5 minutes. After the color development reaction was stopped with 2 M sulfuric acid solution, the OD value was measured.

Figure 6:
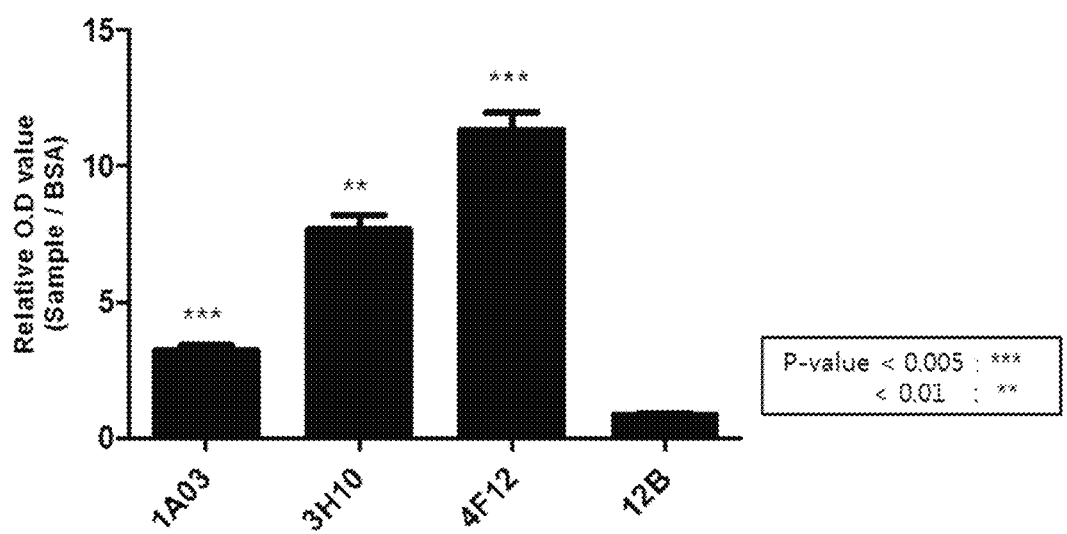
FIG. 6 shows ELISA results illustrating the binding affinity of the three anti-NRP1 scFv antibodies to NRP1.

As a result, 1A03, 3H10 and 4F12 scFv showed specific binding ability to NRP1 as compared to 12B scFv not binding to NRP1 (See FIG. 6).

Figure 7:
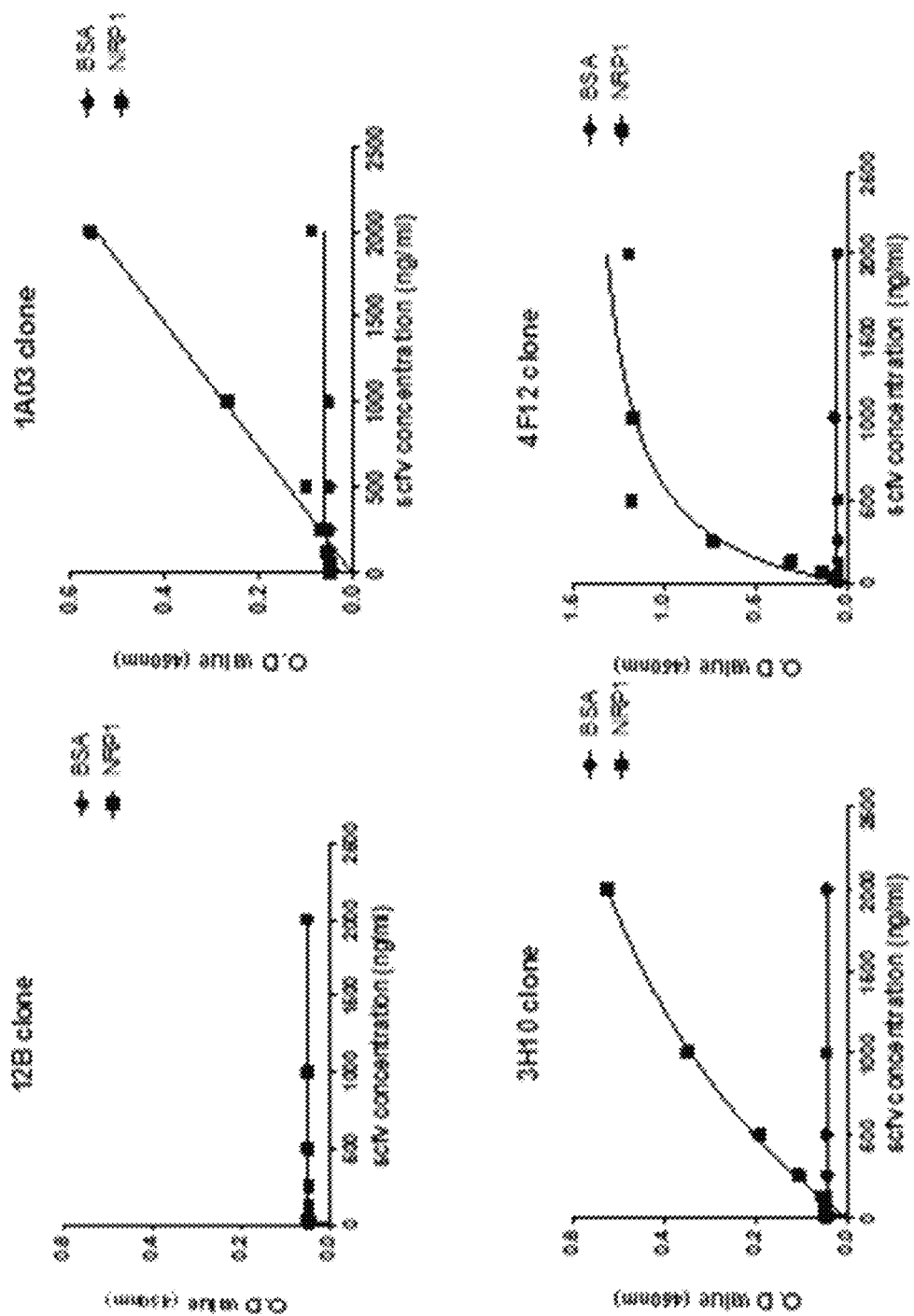
FIG. 7 shows ELISA results illustrating the binding affinity to NRP1 according to the concentrations of the three anti-NRP1 antibody fragments.

Next, in order to measure the binding ability according to the concentration of each antibody fragment to human NRP1, each scFv was inoculated in a concentration of 2,000 ng/ml, 1,000 ng/ml, 500 ng/ml, 250 ng/ml, 125 ng/ml, 62.5 ng/ml, 31.25 ng/ml, or 15.62 ng/ml to 96 wells in which 200 ng of NRP1 or BSA was coated. Then the change in the OD values was analyzed. Regarding the binding ability to NRP1, the OD value of 12B scFv was not changed according to the concentration change. On the other hand, it was conformed that the scFv bound to NRP1 increased with compared to BSA with increasing concentration in the case of 1A03, 3H10 and 4F12 scFvs by change in the OD values (See FIG. 7).

Figure 8:
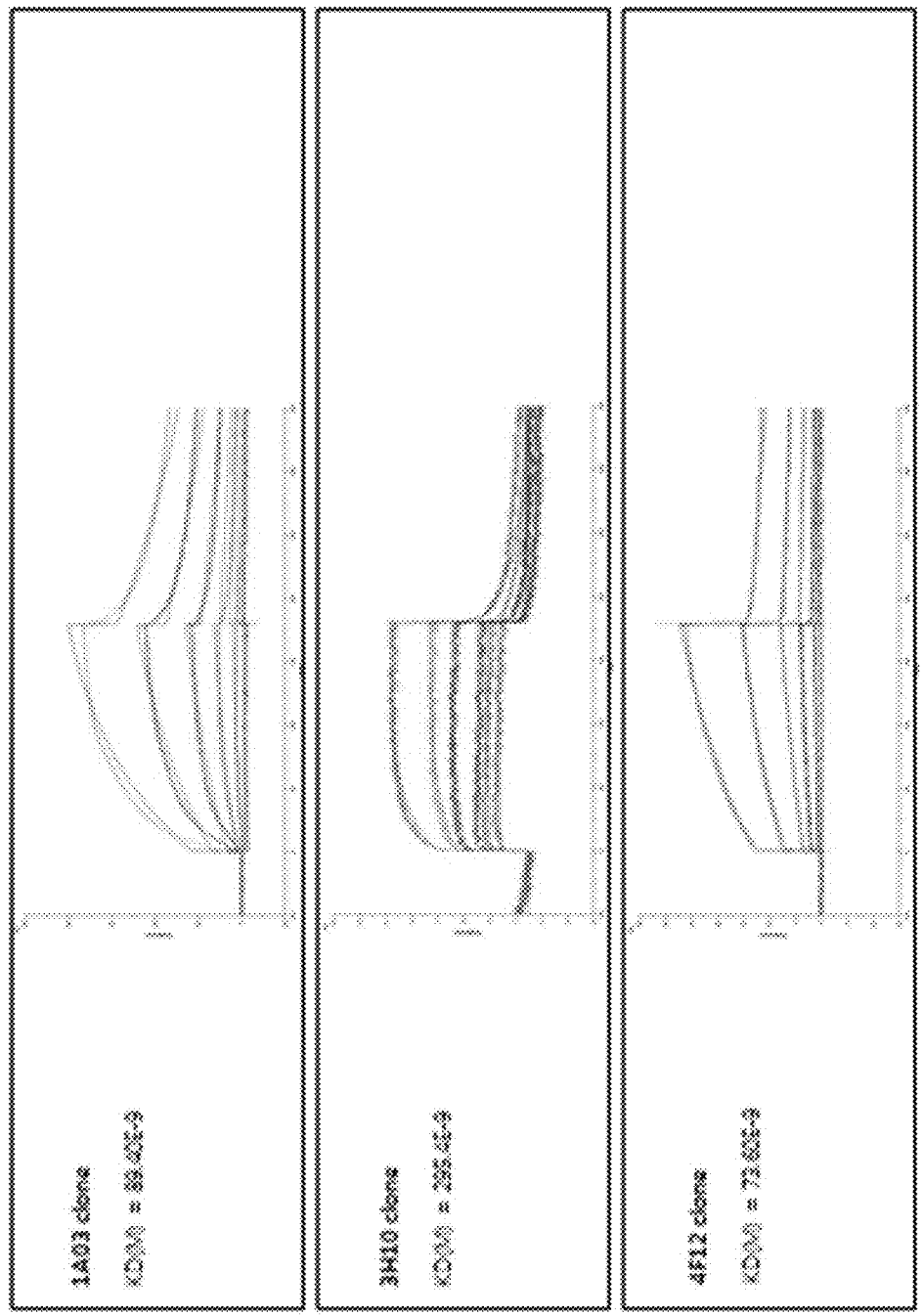
FIG. 8 shows the results illustrating the KD values of the three anti-NRP1 scFv antibodies through SPR analysis.

To accurately measure a degree of the binding ability of the three scFv antibody fragments to NRP1 protein, the final KD value was obtained through ka and kd values using biacore T100, a surface plasmon resonance (SPR) instrument. The KD value is the value obtained by dividing the kd value by the ka value. The lower the KD value, the greater the binding ability to the corresponding substance. As an analysis result, the KD (M) value of the 4F12 scFv was the lowest at $73.60 \times 10^{-9}$. The KD (M) value of the 1A03 scFv was $89.40 \times 10^{-9}$, and the KD (M) value of the 3H10 scFv was $295.4 \times 10^{-9}$ (See FIG. 8).

Example 4

Confirmation of Anti-NRP1 scFv Binding Ability Using NRP1-Overexpressing Cell Lines After binding ability to human NRP1 protein was confirmed by ELISA, FACS analysis was performed using patient-derived cells with high expression of NRP1 in order to determine whether it binds to NRP1 present in the actual cell membrane.

Each scFv was bound to $5 \times 10^5$ of patient-derived cells at 4° C. for approximately 1 hour and then washed 3 times with 1 ml of FACS solution. Then, the result was treated with 1 μg of HA antibody conjugated with red fluorescence (PE; phycoerithrin), and they were bound at 4° C. for 30 minutes. The result was washed three times with 1 ml of FACS solution and was analyzed using a FACS Calibur™ system.

Figure 9:
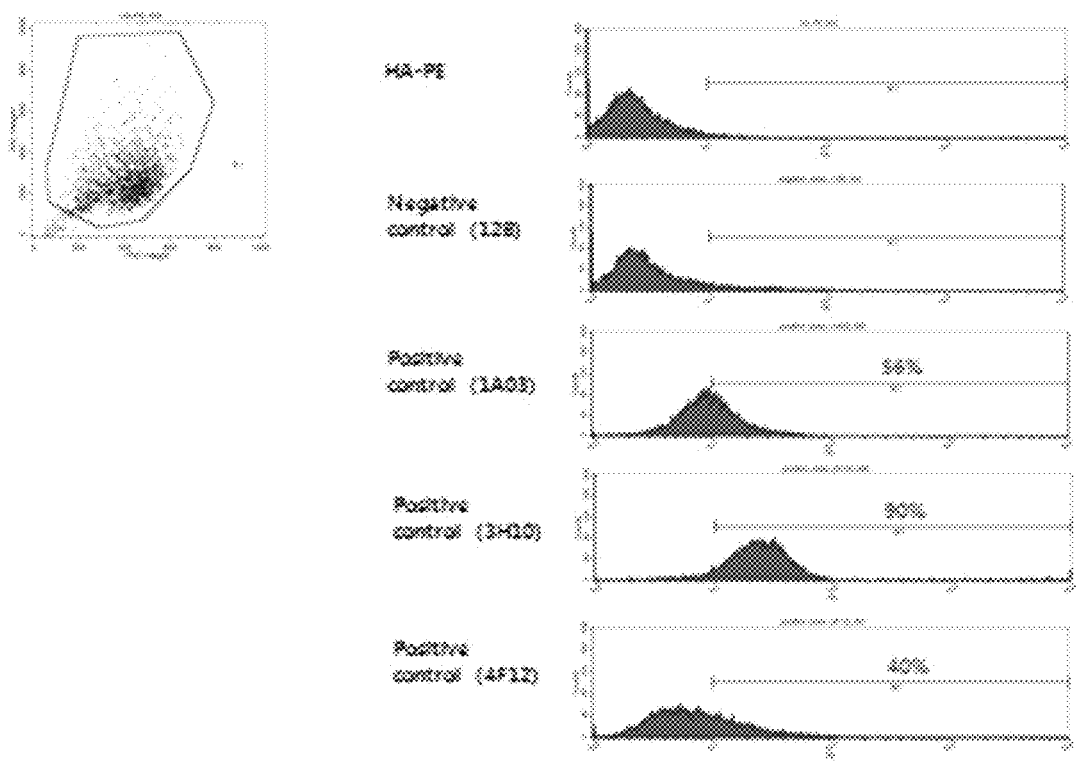
FIG. 9 shows FACS analysis results illustrating the binding affinity of an anti-NRP1 scFv antibody fragment to NRP1-overexpressing patient-derived cells.

As a result of the analysis, three kinds of scFv antibody fragments, such as 1A03, 3H10 and 4F12, specifically bind to NRP1 overexpressed cell lines compared with PE-conjugated HA antibody and 12B treated cells (See FIG. 9).

Example 5

Confirmation of Permeability of Anti-NRP1 scFv into NRP1-Overexpressed Cancer Cells Regarding three anti-NRP1 antibody fragments, the intracellular permeability was confirmed by a cell immunofluorescence staining method. The PD-lysine solution was added to the chamber slide and coated at room temperature for 1 hour to 2 hours. The slide was then dried after removing the solution. Thereafter, 200 μl of NBA solution containing $5 \times 10^4$ of patient-derived cells were treated to slides and then incubated at 37° C. for 4 hours to 5 hours to fix the same to the slide. Next, the NBA solution was removed, and 4% paraformaldehyde was added to fix the same at 4° C. for 10 minutes. After washing three times with PBS, 0.1% of Triton X-100 was treated to increase cell permeability. In order to stain the NRP1 protein, the anti-human NRP1 antibody (R&D) and the anti-NRP1 antibody fragment were simultaneously treated to be bound at 37° C. during a period divided in 15/30/60 minutes. After washing three times with PBS, non-specific binding was blocked with 1% of BSA solution at room temperature for 1 hour. As a secondary antibody, a goat anti-mouse antibody (Invitrogen) labeled with green fluorescence (Alexa-Fluor 488) was treated to examine the NRP1 protein, and an anti-HA antibody (Santacruz biotechnology) was treated to examine the anti-NPR1 antibody fragment so as to bind at room temperature for 1 hour. Finally, DAPI staining was performed for nuclear staining. After final washing, the glass cover was fixed on the slide. The result was observed using a confocal laser scanning microscope.

As a result, in all of the three anti-NRP1 antibody fragments, the anti-NRP1 antibody fragment attached to the surface thereof and the anti-NRP1 antibody fragment inserted into the cell were mixed at 15 minutes and 30 minutes. However, when about 60 minutes elapsed, it was confirmed that most of the anti-NRP1 antibody fragments were penetrated into the cells to be inserted (See FIGS. 10a to 10c). In particular, the 4F12 antibody fragments, rather than the 1A03 and 3H10 antibodies, exhibited relatively high cell permeability according to the time change (See FIG. 10a). These results showed that the antibody of the present disclosure can be used for the purpose of delivering a substance or a therapeutic/diagnostic chemical drug for inhibiting specific protein expression into cancer cells.

Example 6

Confirmation of Inhibition Ability of Cancer Cell Migration of scFv Antibody Fragments for NRP1-overexpressed Cancer Cell Lines Cell migration analysis was performed to test the anticancer ability for inhibiting the movement of cancer cells by the 1A03, 3H10 and 4F12 scFv antibody fragments identified. In the experiment the U87MG cell line (a glioblastoma cell line) known to express highly NRP1 was used. PLO (Poly-L-Ornithine) was put in a transwell (Corning), and the mixture was coated at room temperature for 30 minutes and then dried naturally. Subsequently, 5×10⁴ of U87MG cells and three anti-NRP1 scFv antibody fragments (50 μg/ml) were placed in a DMEM culture medium without 100 μl of the growth factor to be put in a transwell, and 600 μl of a DMEM culture medium with 10% FBS (Fetal Bovine Serum) was placed in a lower well. Then the cells were cultured overnight at 37° C. Subsequently, for 12 wells, methanol, hematoxylin, and eosin (600 μl) were prepared in one per transwell, and then the transwell was left in methanol for 1 minute, followed by hematoxylin for 5 minutes to stain the nuclei. Then, after washing with water, the water was removed, and then the transwell left in eosin for 30 seconds to stain the cytoplasm, then washed again with water, and wiped cleanly inside of the transwell with a cotton swab.

Figure 11:
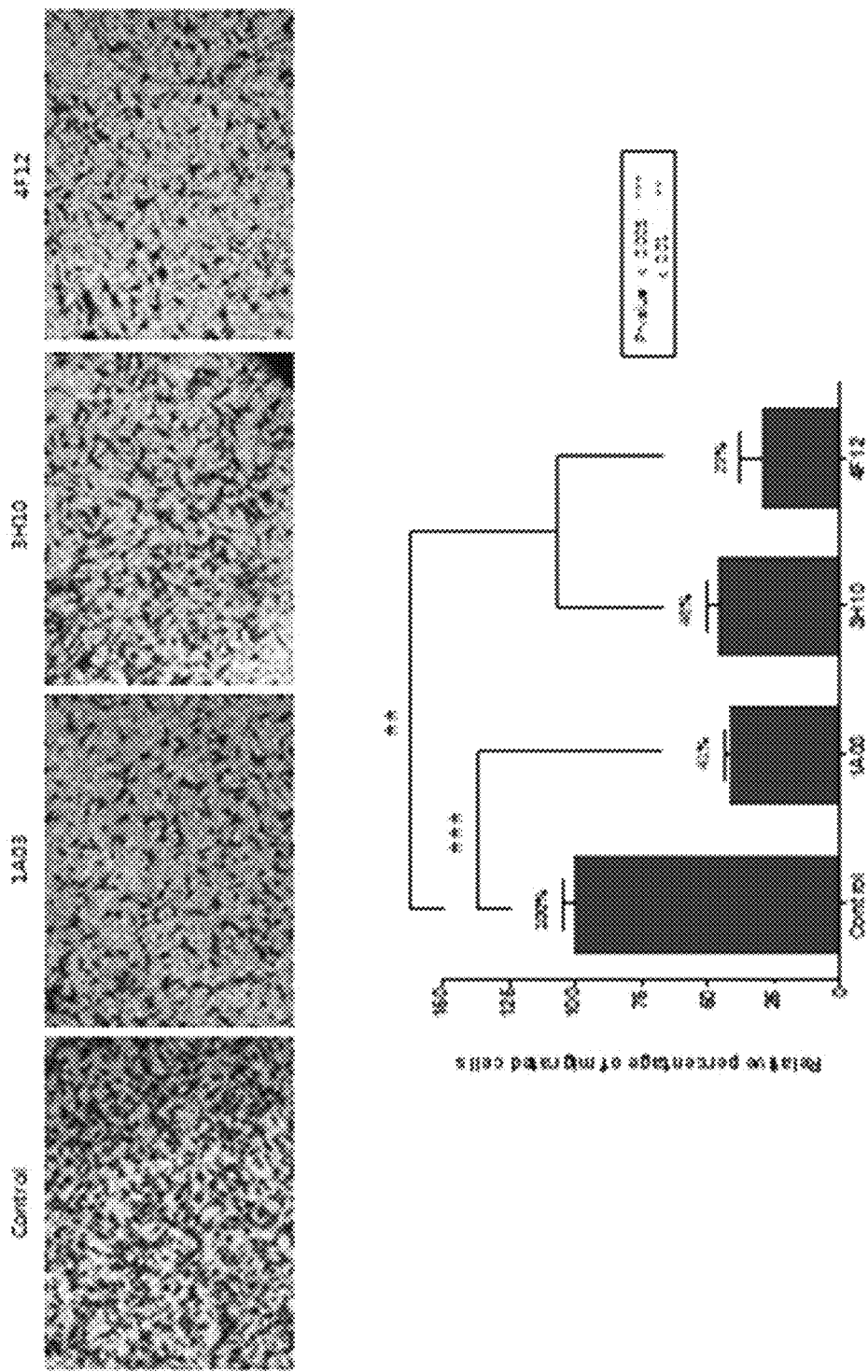
FIG. 11 shows the results of inhibiting cell migration of anti-NRP1 scFv antibody fragments using U87MG cell line.

FIG. 11 shows that the nucleus was stained in dark blue with hematoxylin and the cytoplasm was redded by eosin. As shown in FIG. 11, when the control group in which the anti-NRP1 scFv antibody fragment was not treated was deemed to be 100% cell-transferred, it was shown that the cells containing the 1A03 antibody fragment had 41% cell migration, the cells containing the 3H10 antibody fragment had 46% cell migration, and the cells containing the 4F12 antibody fragment had 29% cell migration. These results demonstrate that the three anti-NRP1 antibody fragments can be used as anticancer agents for glioblastoma, lung cancer, pancreatic cancer, etc., which have high expression of NRP1.

Example 7

Transformation from Anti-NRP1 scFv to Anti-NRP1 IgG

Figure 12:
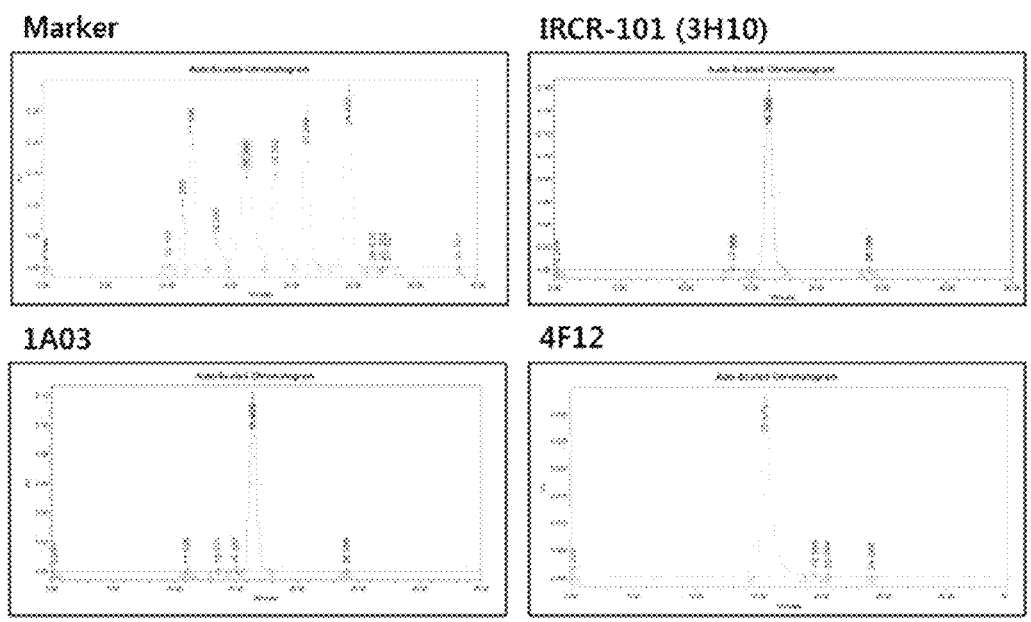
FIG. 12 shows the production purity of three anti-NRP1 IgG antibodies.
Figure 13:
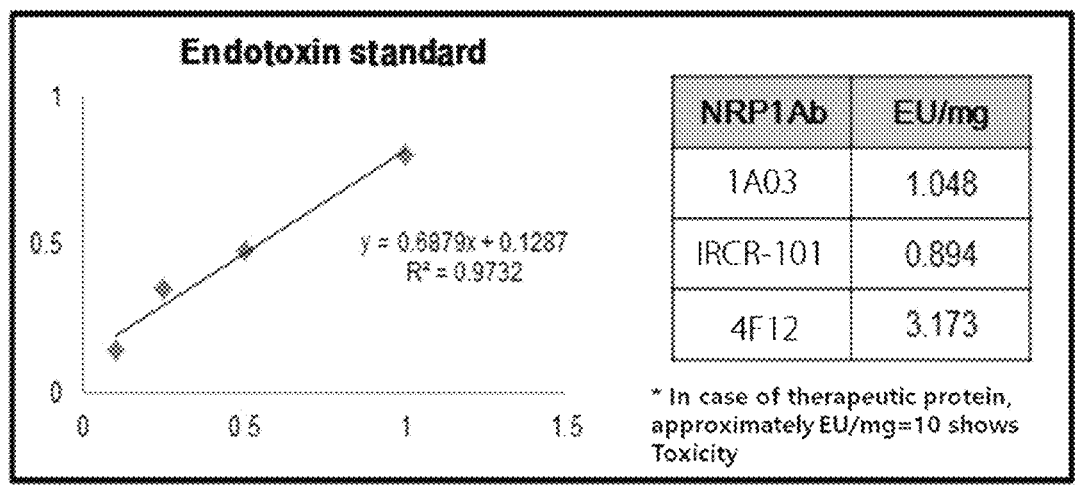
FIG. 13 shows the results of an endotoxin test for three anti-NRP1 IgG antibodies.

In order to transform the anti-NRP1 antibody fragment into IgG form, the gene of the heavy and light chain sequences of NRP1 scFv were transfected using Expi 293F expression system (life technologies). To obtain NRP1 IgG in the culture medium, purification was carried out using an ÄKTA protein purification system and an Amicon centrifugal filter. The yield of IRCR-101 (3H10) was 120 mg/l, A03 was 66 mg/l, and 4F12 was 15 mg/l. In order to confirm the purity of the purified anti-NRP1 antibody, high performance liquid chromatography was introduced. The substance that emerged at 16.388 min at the marker peak was IgG since IgG was 150 kD in size. Three NRP1 antibodies (IRCR-101, 1A03, and 4F12) were detected at this peak, and each purity was 99.5, 99.4, and 99.5% (See FIG. 12). Limulus Amebocyte Lysate (LAL) QCL-1000™ kit was used to determine endotoxin levels of the three NRP1 antibodies produced. As a result, the three kinds of antibodies had about 0.5-3.1 EU/mg corresponding to the normal level of endotoxin of a therapeutic protein (See FIG. 13).

Figure 14:
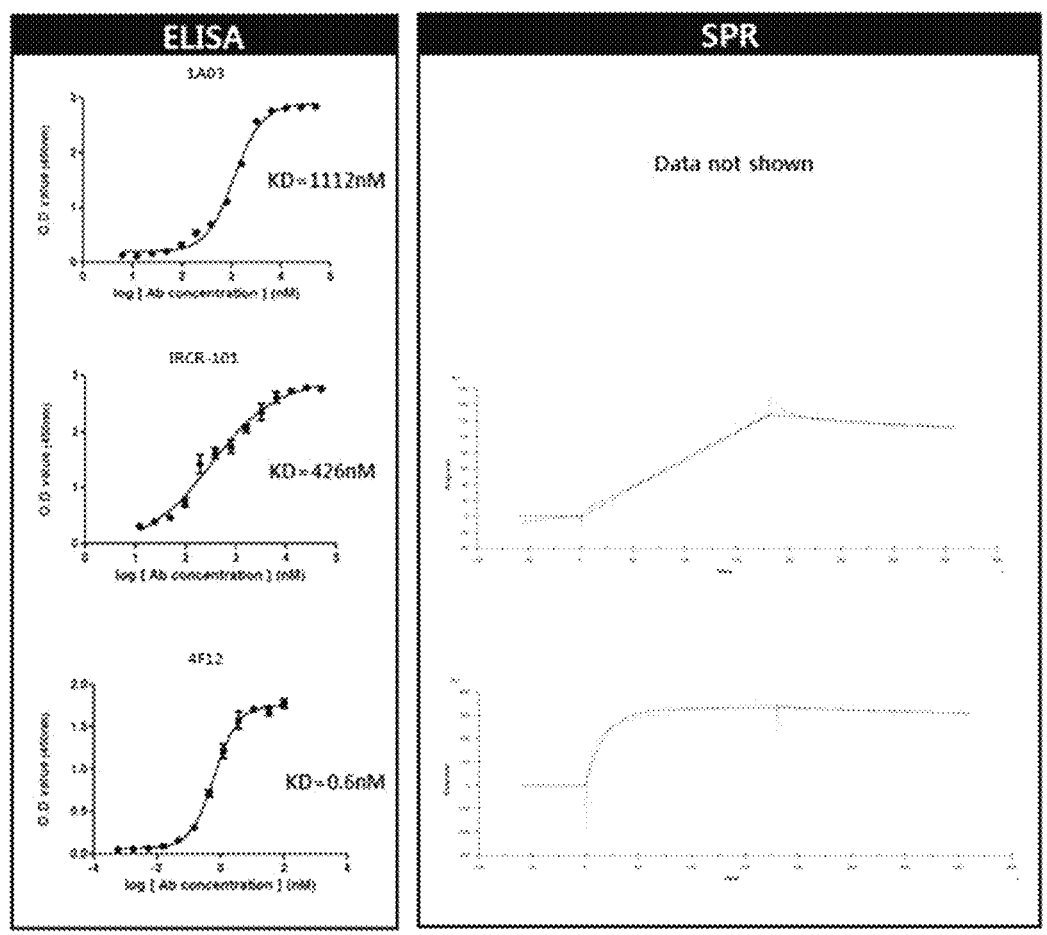
FIG. 14 shows the results of measurement of the KD value of anti-NRP1 IgG using ELISA.
Figure 15:
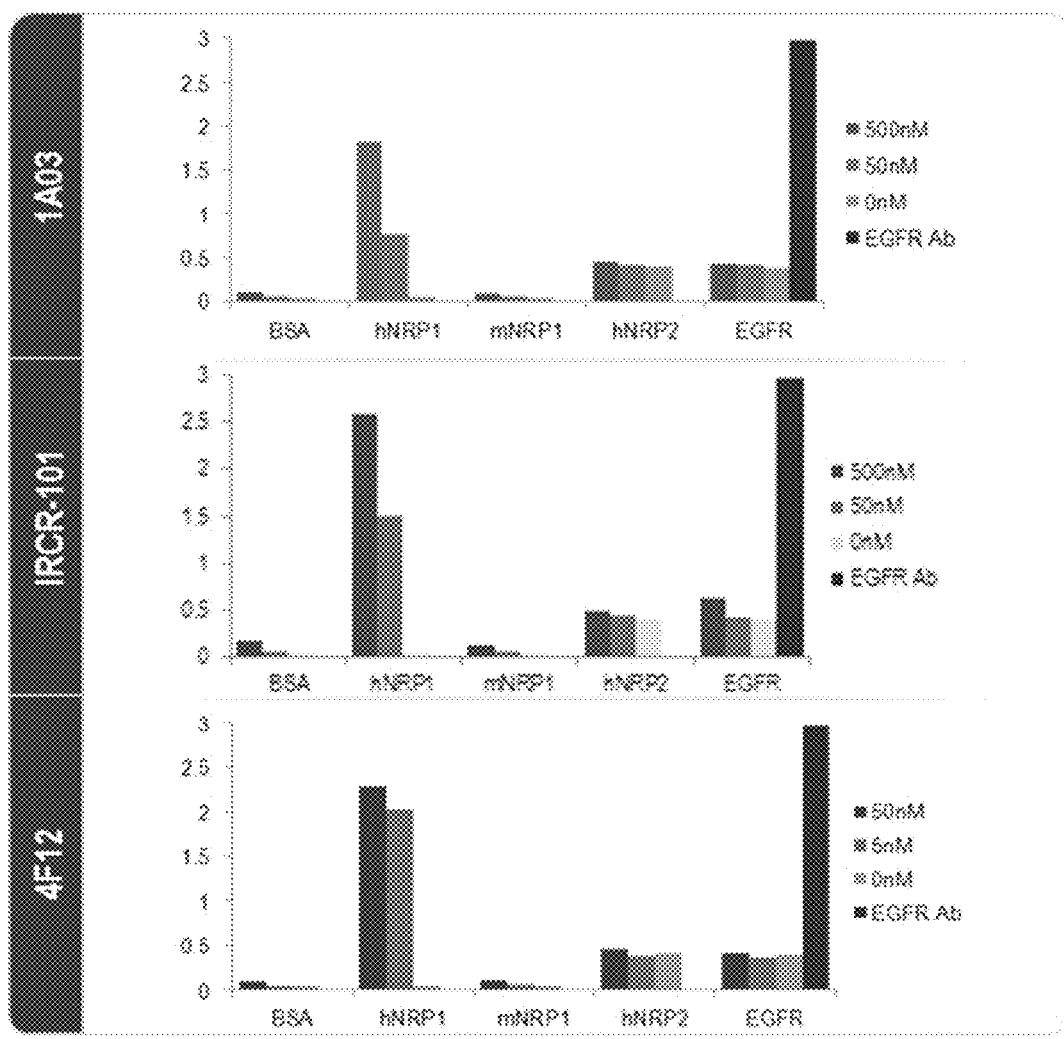
FIG. 15 shows the results of measurement of the specific binding affinity of the three anti-NRP1 IgGs to human NRP1.

Analysis of binding affinity against human NRP1 using the three kinds of NRP1 antibodies through ELISA and SPR analysis revealed that binding affinity was strong in the order of 1A03, IRCR-101, and 4F12. In particular, 4F12 had 0.6 nM of a KD value, which is the binding affinity of the current therapeutic antibody level (See FIG. 14). As a result of analyzing the specific binding affinity to human NRP1 by comparing with other proteins having a structure similar to that of human NRP1, it was confirmed that all three NRP1 antibodies bind only to human NRP1 (See FIG. 15).

Example 8

Figure 16:
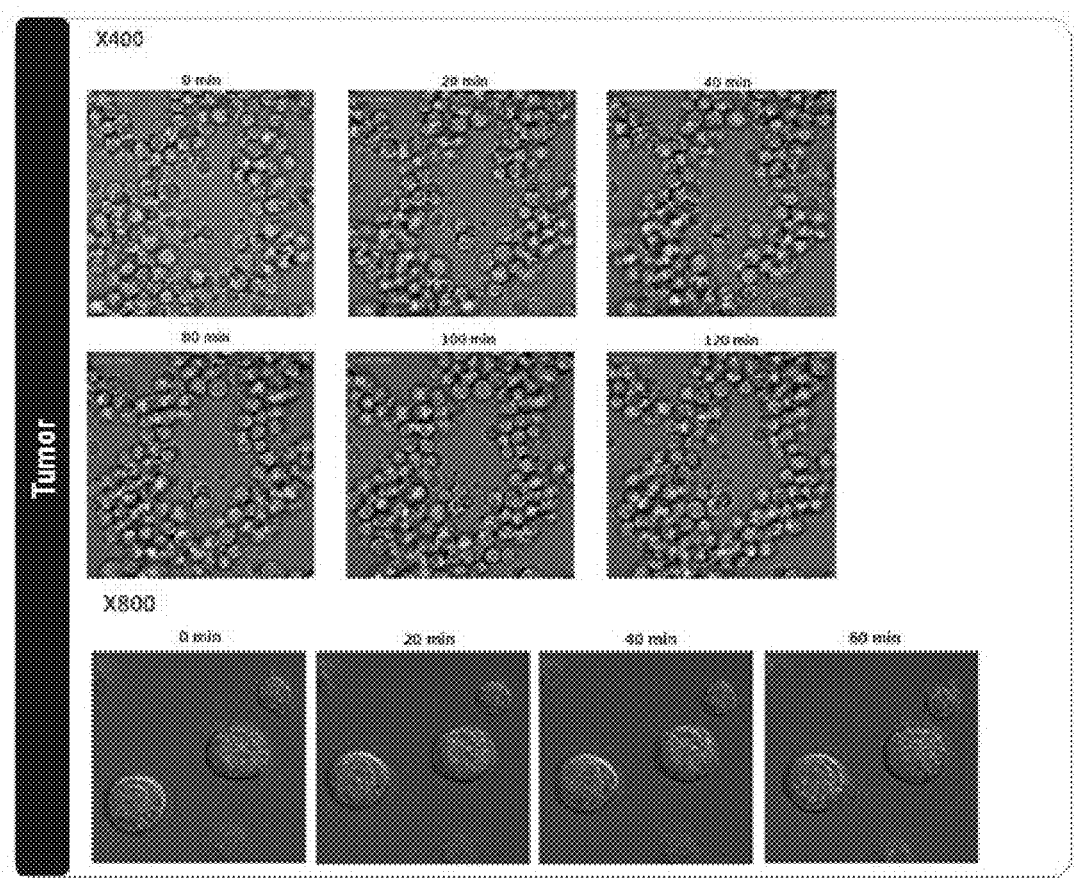
FIG. 16 shows the result of cancer cell-specific internalization using live cell imaging.
Figure 17:
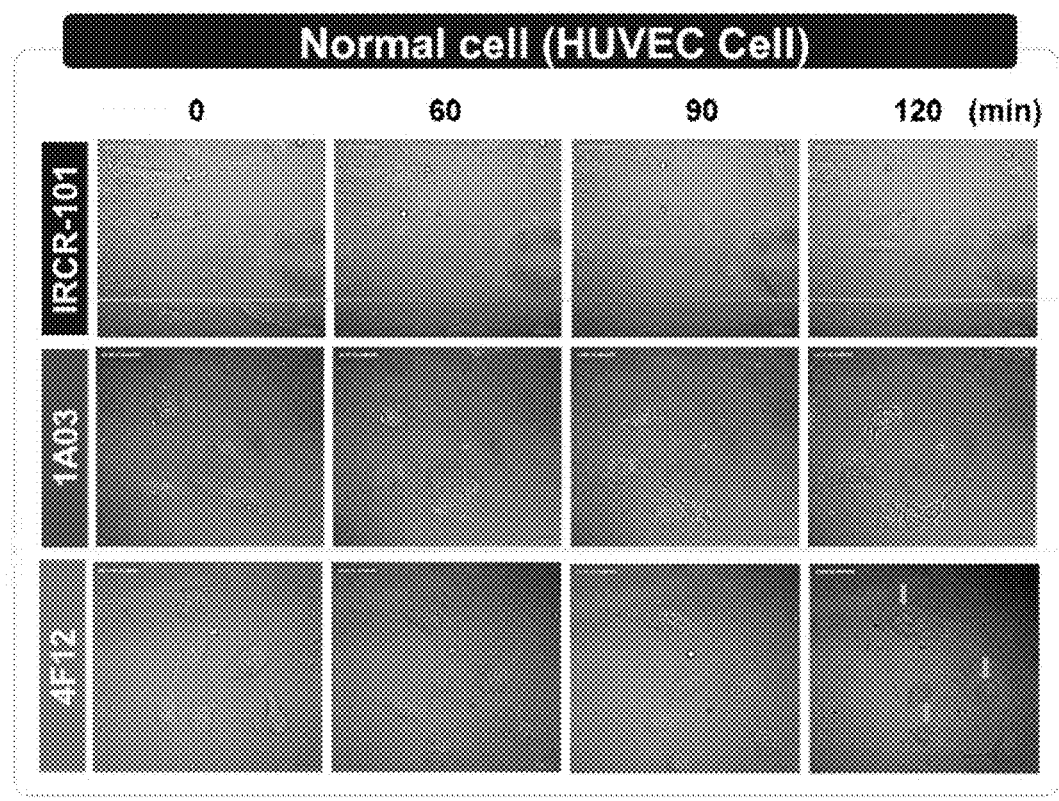
FIG. 17 shows the results of normal cell internalization using live cell imaging.

Confirmation of Cancer-Specific Internalization and Binding Affinity Using Cancer Cells and Normal Cells The internalization of the three anti-NRP1 IgGs in cancer cells and normal cells were compared using the pHrodo® Red Microscale Labeling Kit (Thermo #p35363). The principle of the kit is to conjugate a chromogenic sample to an antibody. When the antibody is outside the cell, it does not develop color. On the other hand, when the antibody is introduced inside the cell to acidify the surrounding environment, it develops color. Thus, the internalization of the antibody can be confirmed using the such principle of color development. Patient-derived cancer cells and HUVEC cells, which are normal cells, respectively, conjugated to the three kinds of NRP1 IgG were used to compare internalization from each other. As a result, internalized antibodies were observed on the patient-derived cancer cells from 20 minutes (See FIG. 16). On the other hand, in HUVEC cells that are normal cells, 4F12 showed internalization of antibodies after 2 hour elapsed, and IRCR-101 and 1A03 antibodies did not show any internalized antibody. Thus, it was confirmed that the IRCR-101 and 1A03 antibodies exhibited cancer cell-specific internalization (See FIG. 17).

Figure 18:
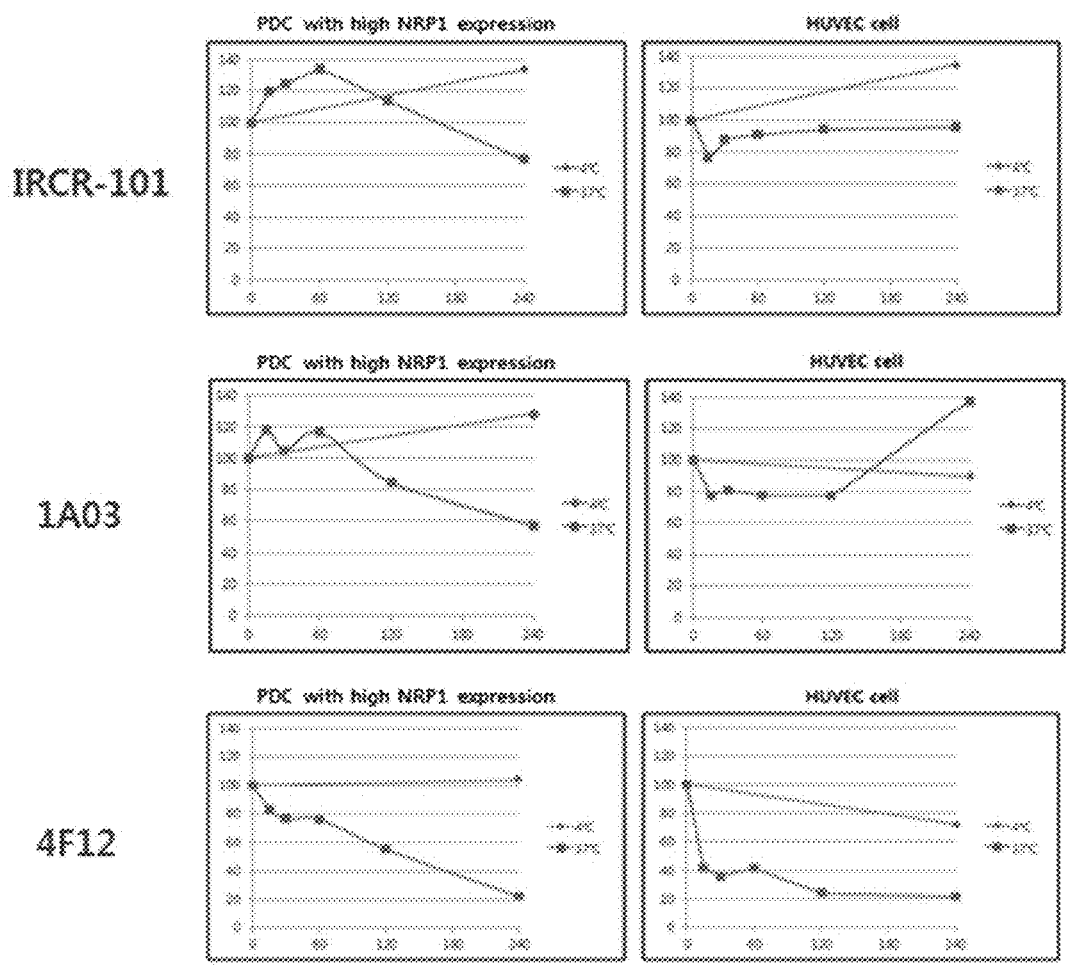
FIG. 18 shows the result of cancer cell-specific internalization using FACS.

The binding at 4° C. and 37° C. (internalizing temperature) for normal and cancer cells was compared from each other and was analyzed by FACS. The IRCR-101 and 1A03 antibodies did not show any increase or decrease in the amount of the antibodies on the cell surface over time because of the absence of internalization in normal cells and cancer cells at 4° C. On the other hand, it was confirmed that the amount of the antibodies on the cell surface was decreased with time as it was internalized only in cancer cells at 37° C. On the other hand, the 4F12 antibody was internalized in normal cells and cancer cells at 37° C., and the amount of antibody on the cell surface was decreased with time (See FIG. 18). Thus, it was confirmed that IRCR-101 and 1A03 antibodies each had a cancer specific internalizing function by live cell imaging and FACS analysis.

Figure 19:
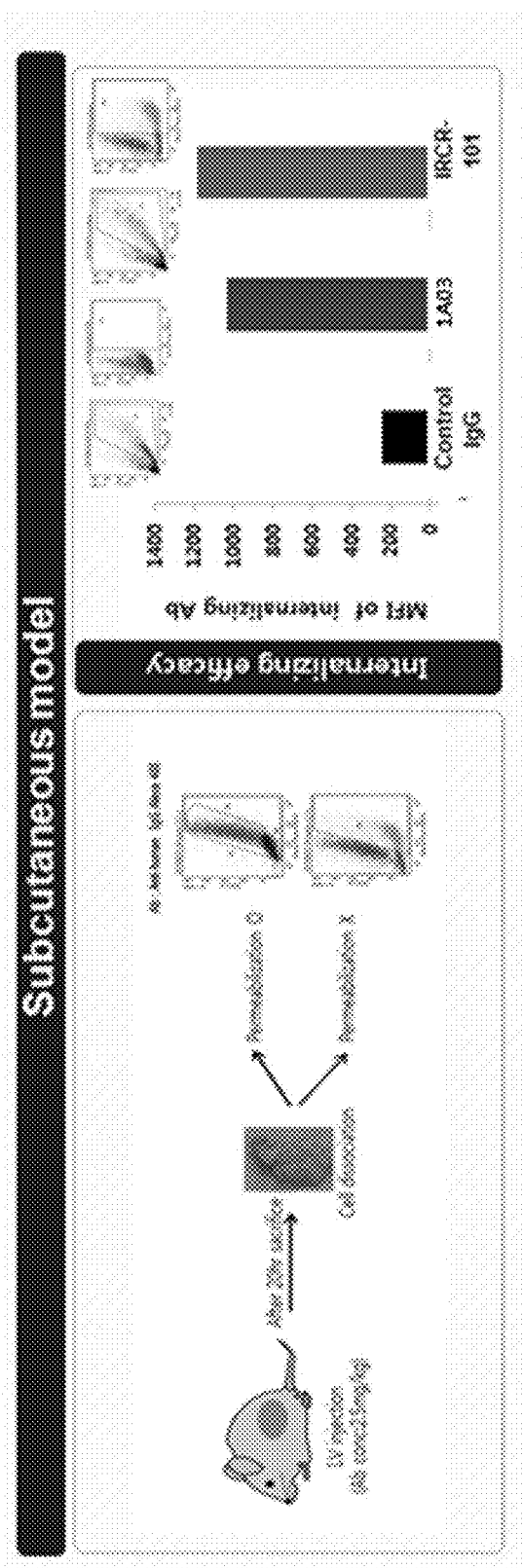
FIG. 19 shows the results of internalization of IRCR-101 in a glioblastoma subcutaneous model.

Control IgG, IRCR-101, and 1A03 were injected in a glioblastoma subcutaneous model by an intravenous injection. After 20 hours, they were sacrificed to separate into a single cell through cell dissociation. Then immanence thereof to cancer cells were compared from each other using FACS. In the results of screening only antibodies internalizing into cancer cells through permeabilization, IRCR-101 and 1A03 showed 5 times to 6 times higher mean fluorescence intensity (MFI) than the control IgG. It was also confirmed that the in vivo model had cancer cells-specified immanence as in vitro model as described above. (See FIG. 19).

Figure 20:
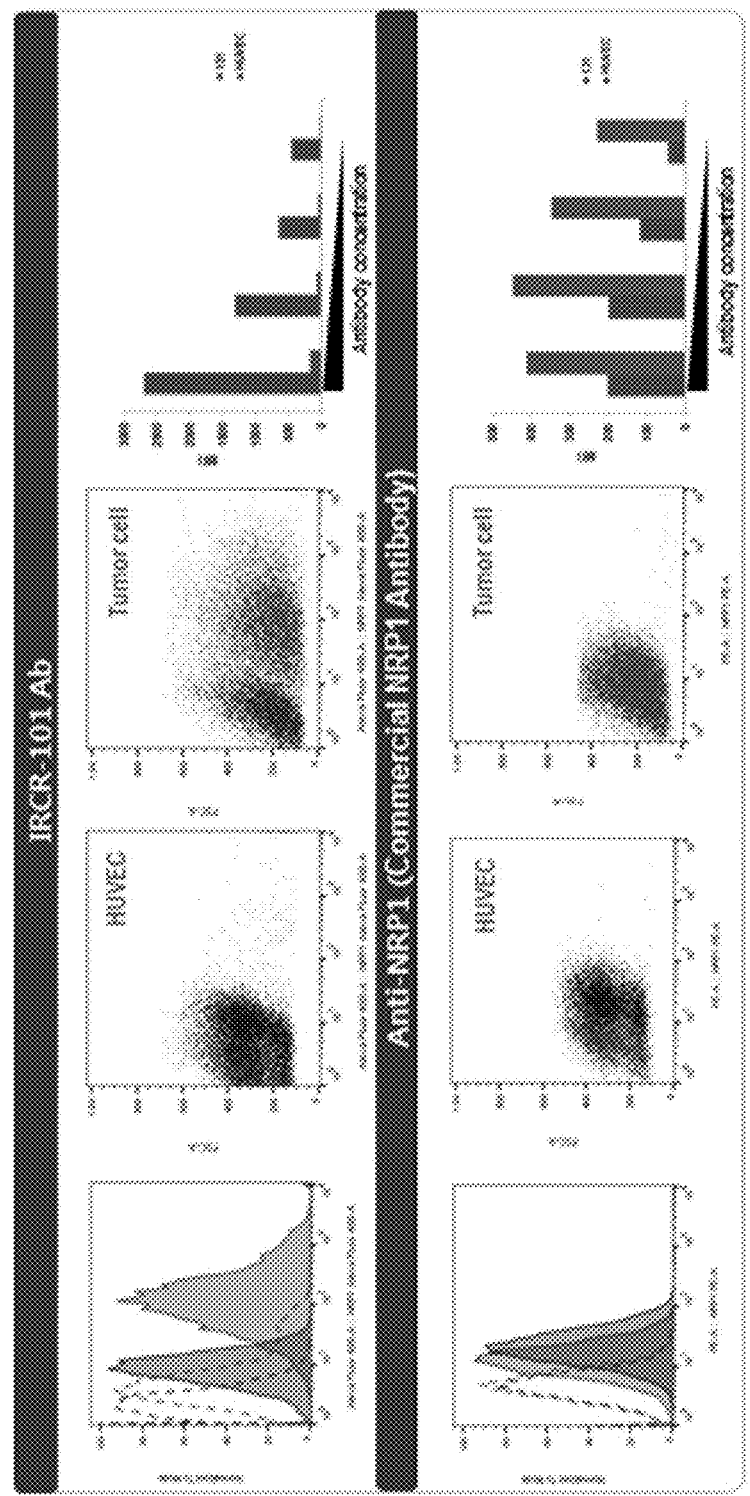
FIG. 20 shows the cancer cell-specific binding ability of IRCR-101.

IRCR-101 and NRP1 antibodies were used at 4° C. to compare the difference in binding force between normal and cancer cells. At the same concentration, the conventional NRP1 antibody showed a greater binding affinity to the normal cells compared to the cancer cells, while the IRCR-101 showed cancer cell-specific binding ability (See FIG. 20).

Figure 21:
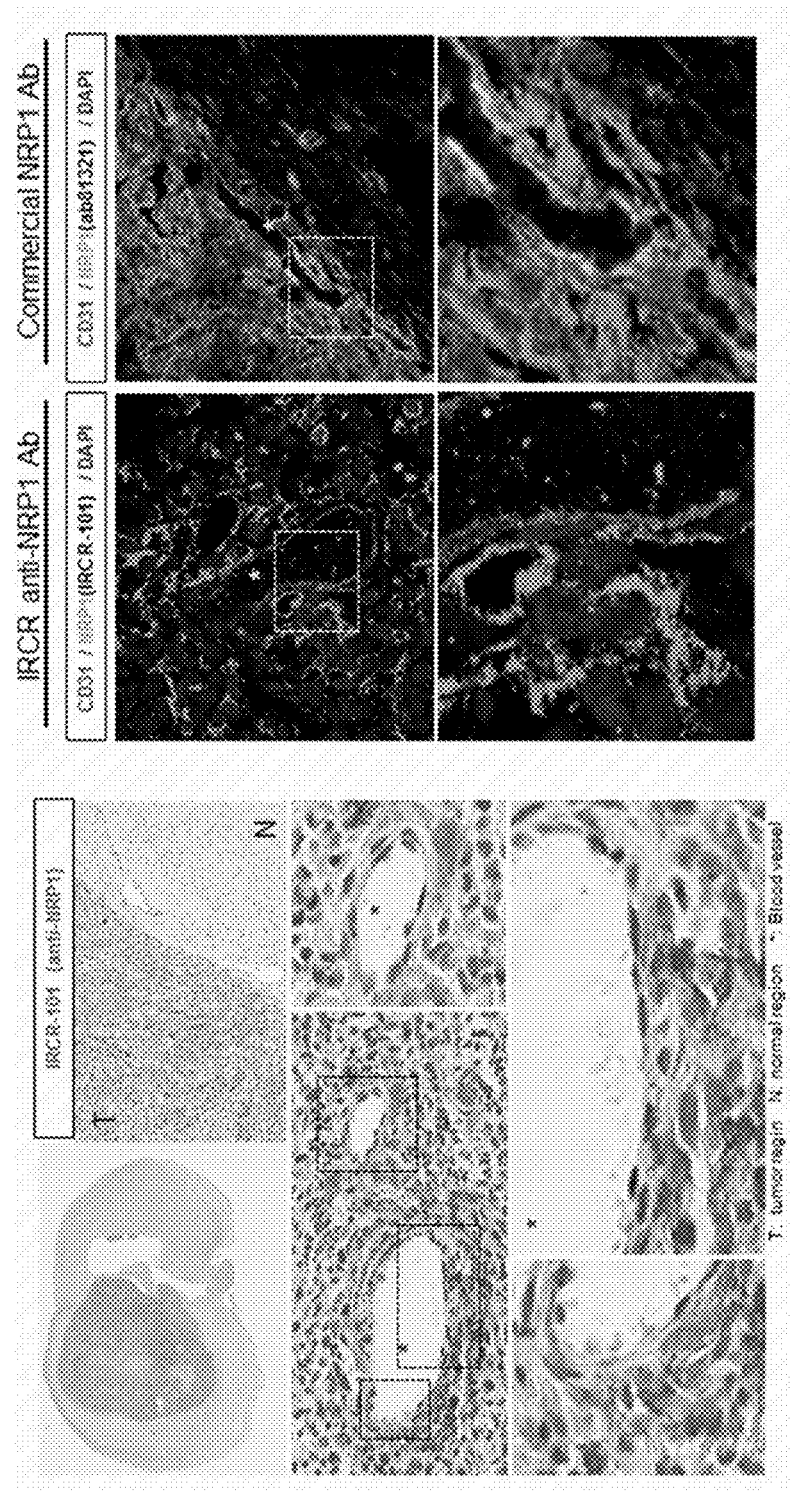
FIG. 21 shows the binding ability of IRCR-101 to cancer-specific NRP1 in a glioblastoma xenograft model.
Figure 22:
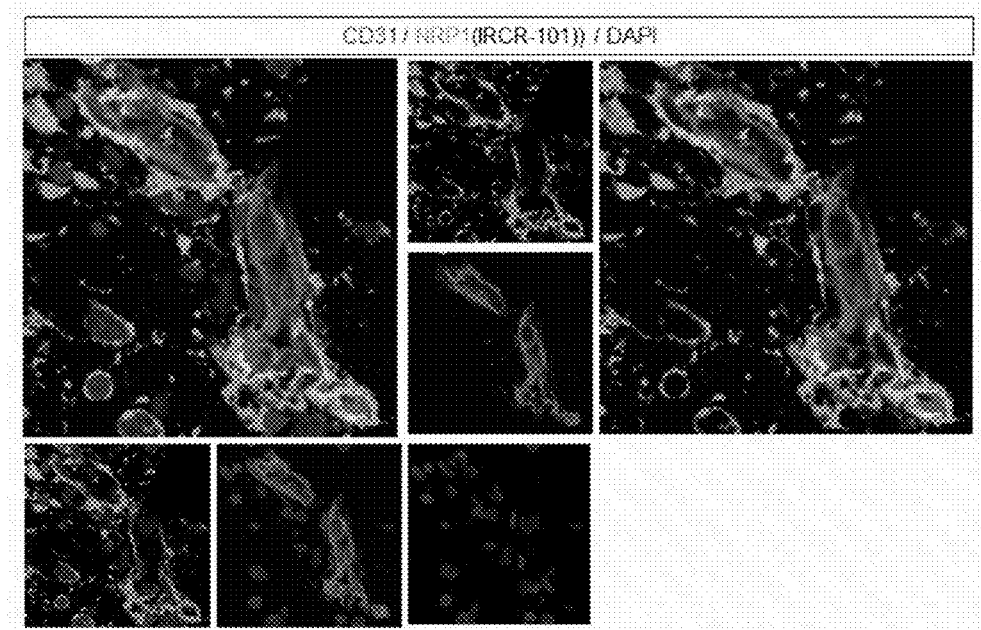
FIG. 22 shows the binding ability of IRCR-101 to cancer-specific NRP1 in a glioblastoma patient sample.

In order to confirm whether it was reproduced in the in vivo model, IHC (Immunohistochemistry) and IF (Immunofluorescence) were analyzed using the cancer tissue obtained from the glioblastoma xenograft. The conventional NRP1 antibody showed binding force to blood vessels composed of normal endothelial cells whereas IRCR-101 did not bind to normal endothelial cells (See FIG. 21). This was also observed in glioblastoma patient tissues (See FIG. 22).

Example 9

Confirmation of Inhibition of Cancer Cell Migration and Neovascular Growth

Figure 23:
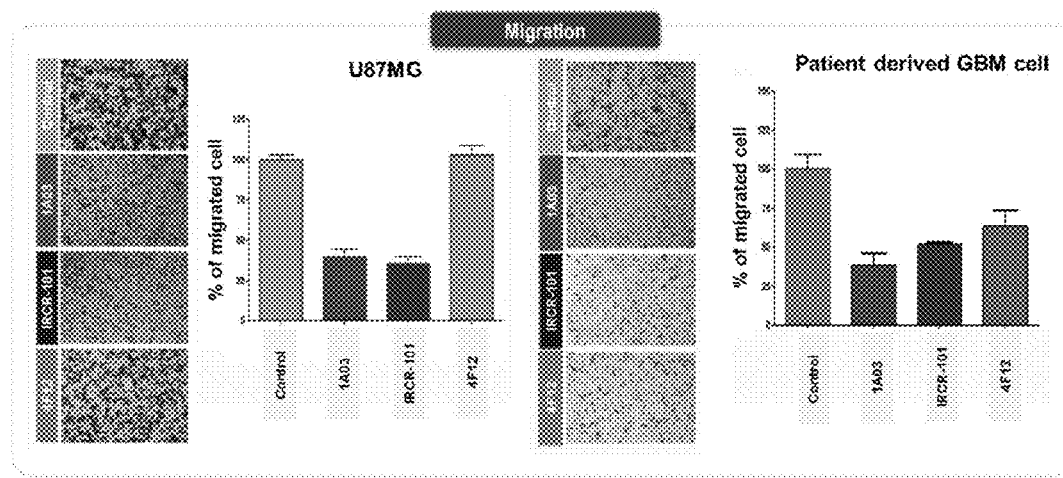
FIG. 23 shows the results of cell migration suppression ability using a glioblastoma cell line U87MG and patient-derived cells.

It was confirmed that the three NRP1 antibodies inhibited cancer cell migration using the glioblastoma cell line U87MG and patient-derived cells. After each antibody treatment, the cells were incubated at 37° C. for 24 hours. It was confirmed that IRCR-101 and 1A03 each inhibited more than 50% of tumor cells migration and 4F12 inhibited 40% of tumor cells migration in the patient-derived cells (See FIG. 23).

Figure 24:
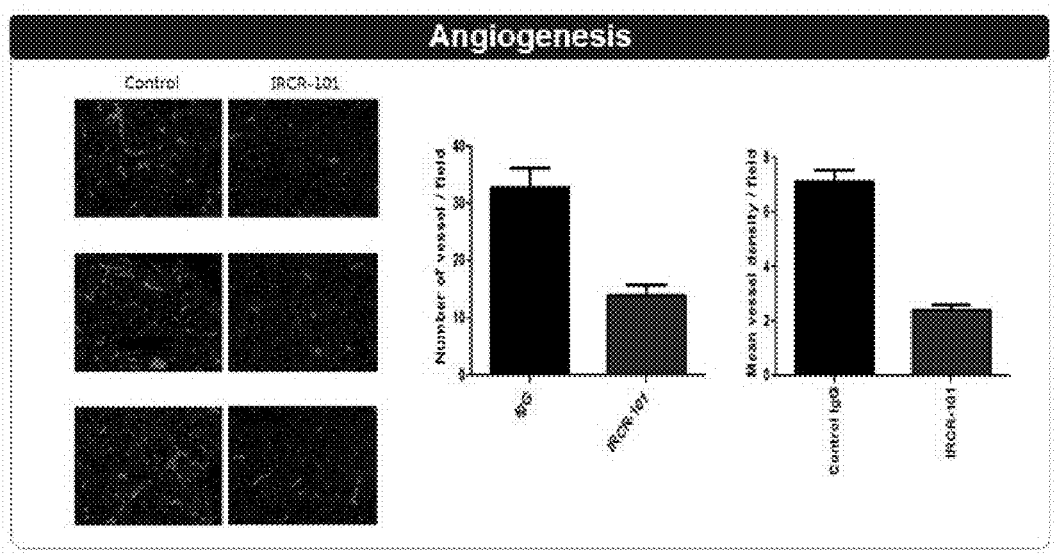
FIG. 24 shows the results of inhibitory effect of IRCR-101 on neovascularization in a glioblastoma subcutaneous model.

In the subcutaneous model of glioblastoma, IRCR-101 was injected intravenously for 2 weeks, and then it was examined whether CD31 changes were associated with neovascularization. CD31 was significantly decreased compared to the control group, and both the number and the thickness of blood vessels were decreased. Thus, it was confirmed that IRCR-101 inhibited neovascularization in the in vivo model in addition to cell migration ability in glioblastoma (See FIG. 24).

Figure 25:
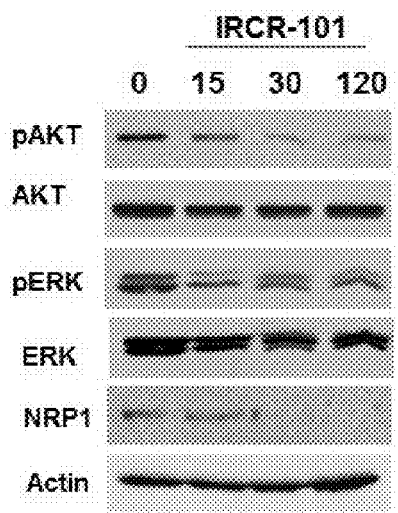
FIG. 25 shows the results of the change of the downstream signaling involved in the IRCR-101 treatment.

Immunoblotting of NRP1, AKT, and ERK at 15, 30 and 120 min was performed in order to examine the change of the related signal transmission material in IRCR-101 treatment. It was confirmed that NRP1 was completely degraded to be eliminated after 30 minutes and AKT and ERK inhibited the related signal mechanism since the phosphorylated AKT and ERK decreased (See FIG. 25).

Example 10

IRCR-101 Distribution Confirmation and Monkey TMA Analysis of In Vivo Model

Figure 26:
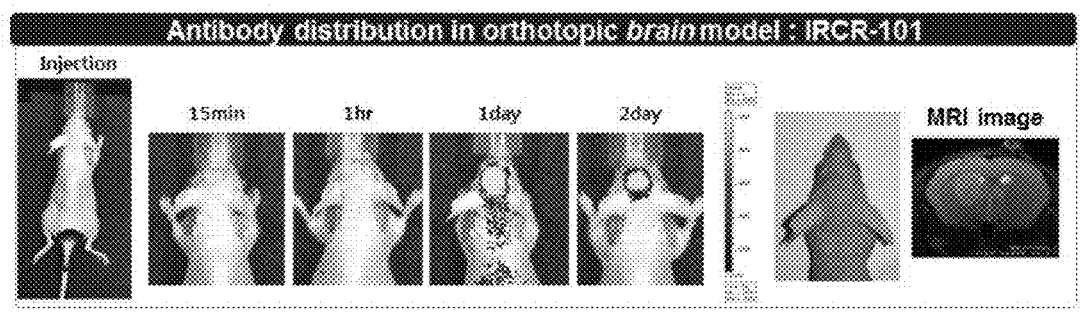
FIG. 26 shows the distribution of IRCR-101 in a glioblastoma orthotopic model.

In the orthotopic model of the glioblastoma, the fluorescent substance was labeled with IRCR-101 and the cells were injected intravenously to observe the fluorescence intensity change with time. The observation was carried out at 15 minutes, 1 hour, 1 day, and 2 days. As a result, it was confirmed that the fluorescence developed strongly at the site corresponding to the tumor site at 1 day, and fluorescence had developed at the same position until 3 days (See FIG. 26).

Figure 27:
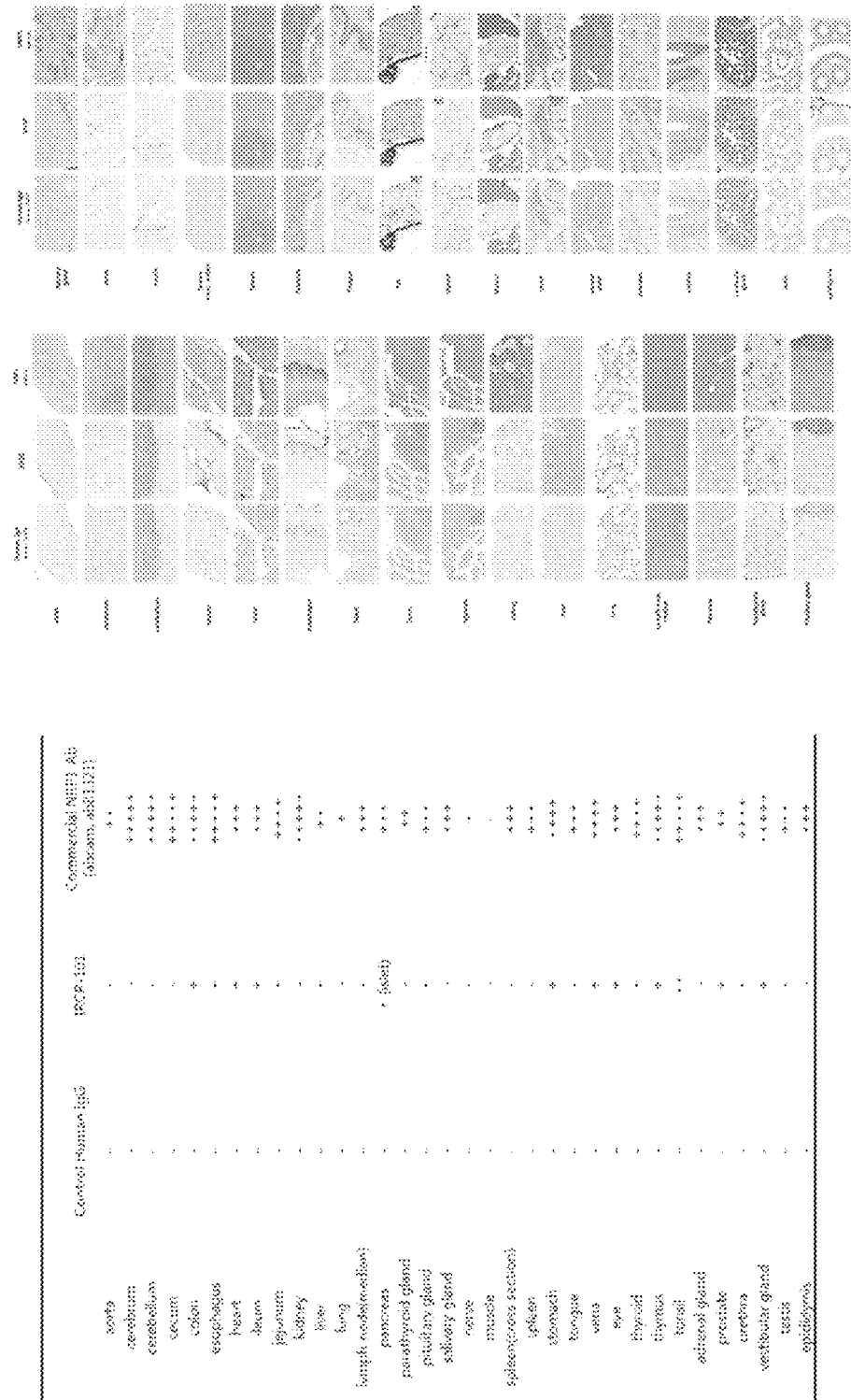
FIG. 27 shows the results of analysis of male and female monkeys TMA.

TMA (Tissue microarray) of male and female monkeys as well as the conventional NRP1 antibody were performed in order to investigate the side-effect of IRCR-101. The analysis showed that most of the normal organ tissues showed less or no binding of the IRCR-101 antibody than the conventional NRP1 antibody. Therefore, it is predicted that the side-effect of IRCR-101 is low in clinical trials as it shows low or almost no binding affinity to normal tissues. (See FIG. 27).

INDUSTRIAL APPLICABILITY

The features and advantages of the present disclosure are summarized as follows:

(i) The present disclosure provides anti-NRP1 antibodies and medicinal uses thereof, which bind to NRP1 expressed on the surface of cancer cells and then are internalized into the cells.

(ii) The antibody of the present disclosure inhibits invasion and metastasis of cancer cells expressing NRP1.

(iii) The antibody of the present disclosure can be used alone or in the form of an antibody-drug conjugate for treatment of cancers. Since NRP1 is a molecule that is overexpressed on the surface of the cancer cells, the antibody-drug conjugate of the present disclosure is used to selectively target only cancer cells while minimally affecting normal cells.

The specific portions of the present disclosure are described in detail as described above. It will be apparent to those skilled in the art that such specific descriptions are only preferred embodiments and that the scope of the present disclosure is not limited thereby. Accordingly, the actual scope of the present disclosure will be defined by the appended claims and their equivalents.

The invention claimed is:

1. An antibody or an antigen-binding fragment thereof that binds to NRP1, comprising:
 a heavy chain variable region comprising CDRH1, CDRH2, and CDRH3, respectively, comprising sequences of SEQ ID NOS: 1 to 3 and a light chain variable region comprising CDRL1, CDRL2, and CDRL3, respectively, comprising sequences of SEQ ID NO: 4, ANN, and SEQ ID NO: 6;
 a heavy chain variable region comprising CDRH1, CDRH2, and CDRH3, respectively, comprising sequences of SEQ ID NOS: 7 to 9 and a light chain variable region comprising CDRL1, CDRL2, and CDRL3, respectively, comprising sequences of SEQ ID NO: 10, SDN, and SEQ ID NO: 12; or
 a heavy chain variable region comprising CDRH1, CDRH2, and CDRH3, respectively, comprising sequences of SEQ ID NOS: 7, 8, and 13 and a light chain variable region comprising CDRL1, CDRL2, and CDRL3, respectively, comprising sequences of SEQ ID NO: 10, SDS, and SEQ ID NO: 15.

2. The antibody or antigen-binding fragment thereof according to claim 1, comprising a heavy chain variable region comprising heavy chain framework region (FR) comprising one sequence selected from the group consisting of sequences of SEQ ID NOS: 28 to 33.

3. The antibody or antigen-binding fragment thereof according to claim 1, comprising a light chain variable region comprising a light chain framework region (FR) comprising one sequence selected from the group consisting of sequences of SEQ ID NOS: 34 to 42.

4. The antibody or antigen-binding fragment thereof according to claim 1, comprising a heavy chain variable region and a light chain variable region comprising:
 (i) a heavy chain variable region comprising a sequence of SEQ ID NO: 16 and a light chain variable region comprising a sequence of SEQ ID NO: 17;
 (ii) a heavy chain variable region comprising a sequence of SEQ ID NO: 18 and a light chain variable region comprising a sequence of SEQ ID NO: 19; or
 (iii) a heavy chain variable region comprising a sequence of SEQ ID NO: 20 and a light chain variable region comprising a sequence of SEQ ID NO: 21.

5. A nucleic acid encoding the antibody or antigen-binding fragment thereof according to claim 1.

6. A vector comprising the nucleic acid according to claim 5.

7. A cell transformed with the vector according to claim 6.

8. A method of producing an antibody or an antigen-binding fragment thereof binding to NRP1, comprising: (a) culturing the cell of claim 7; and (b) recovering the antibody or antigen-binding fragment thereof from the cultured cell.

9. An antibody-drug conjugate comprising the antibody or antigen-binding fragment thereof according to claim 1, and a drug.

10. A composition for preventing or treating a cancer comprising the antibody or antigen-binding fragment thereof according to claim 1, or an antibody-drug conjugate comprising the antibody or antigen-binding fragment thereof, and a drug, as an active ingredient.

11. The composition according to claim 10, wherein the cancer is selected from the group consisting of glioblastoma, astrocytoma, glioma, neuroblastoma, testicular cancer, colon cancer, melanoma, pancreatic cancer, lung cancer, breast cancer, esophageal cancer, and prostate cancer.

* * * * *